(12) United States Patent
Koide et al.

(10) Patent No.: US 6,939,617 B2
(45) Date of Patent: Sep. 6, 2005

(54) NON-ADHESIVE LATEX PRODUCTS

(75) Inventors: Kazuo Koide, Chiba (JP); Takayuki Suzuki, Chiba (JP); Takahisa Suzuki, Chiba (JP)

(73) Assignee: Suzuki Latex Industry Co., Ltd., Chiba (JP)

(*) Notice: Subject to any disclaimer, the term of this patent is extended or adjusted under 35 U.S.C. 154(b) by 0 days.

(21) Appl. No.: 09/997,467

(22) Filed: Nov. 28, 2001

(65) Prior Publication Data

US 2002/0101007 A1 Aug. 1, 2002

Related U.S. Application Data

(63) Continuation-in-part of application No. PCT/JP00/03370, filed on May 25, 2000.

(30) Foreign Application Priority Data

May 28, 1999 (JP) .............................. 11/149718
Mar. 18, 2000 (JP) ...................................... 2000/121767

(51) Int. Cl.[7] .............................................. B32B 25/00
(52) U.S. Cl. ........................... 428/492; 428/500; 2/168; 525/363
(58) Field of Search ................................ 428/492, 500, 428/35.2, 35.5, 35.7, 36.8; 2/168, 167; 525/363

(56) References Cited

U.S. PATENT DOCUMENTS

| | | | |
|---|---|---|---|
| 2,868,754 A | | 1/1959 | Eilbeck et al. |
| 2,937,164 A | | 5/1960 | Brown et al. |
| 3,639,298 A | | 2/1972 | Lister et al. |
| 3,740,262 A | * | 6/1973 | Agostinelli ............... 427/2.3 |
| 3,740,357 A | | 6/1973 | Wax |
| 3,743,612 A | | 7/1973 | Vial |
| 3,753,941 A | | 8/1973 | Cline et al. |
| 3,767,605 A | | 10/1973 | Gerlicher |
| 4,172,067 A | * | 10/1979 | Benton et al. ............... 521/65 |
| 4,199,490 A | * | 4/1980 | Kamiya et al. ............. 524/501 |
| 4,304,008 A | * | 12/1981 | Joung ............................ 2/167 |
| 5,195,537 A | | 3/1993 | Tillotson |

(Continued)

FOREIGN PATENT DOCUMENTS

| | | |
|---|---|---|
| BE | 547 273 A | 10/1956 |
| DE | 19 06 901 A | 9/1969 |
| EP | 0486183 A1 | 5/1992 |

(Continued)

OTHER PUBLICATIONS

Zakharov, N.D., "Vulcanization of Carboxylic Rubbers," Rubber Chemistry and Technology, Rubber Division ACS, Akron, U.S., 36(3):568–574 (1963).

Brown, H.P., "Crosslinking Reactions Of Carboxylic Elastomers," Rubber Chemistry and Technology, Rubber Division ACS, Akron, U.S., 36(4):931–962 (1963).

*Primary Examiner*—James J. Seidleck
*Assistant Examiner*—Melanie Bissett
(74) *Attorney, Agent, or Firm*—Fish & Richardson P.C.

(57) ABSTRACT

The object of the present invention is to provide a non-adhesive clean latex product and a method for manufacturing the same. A non-adhesive clean emulsion latex product is manufactured by adding a carboxyl-group blocking agent to a carboxylated latex or by providing a layer treated with the carboxyl-group blocking agent on one or both surfaces of a film of the carboxylated latex. Further, a non-adhesive, easy-to-wear-and- remove emulsion latex product is manufactured by affording a layer treated with a carboxyl group blocking agent on the inside surface of a carboxylated latex film and providing a chlorination treatment on the outside thereof. Furthermore, a sulfur free, highly durable latex product can be manufactured by adding an aluminate or an aluminumhydroxide gel to the latex. The present invention also provides a non-powered, clean, on-machine wound fingerstall.

9 Claims, 4 Drawing Sheets

U.S. PATENT DOCUMENTS

| | | | |
|---|---|---|---|
| 5,357,636 A | * 10/1994 | Dresdner et al. | 2/161.7 |
| 5,578,674 A | * 11/1996 | Speth et al. | 524/575 |
| 5,739,203 A | * 4/1998 | Ngoc | 524/527 |
| 5,997,969 A | * 12/1999 | Gardon | 428/35.7 |
| 6,051,107 A | * 4/2000 | Varnell | 439/607 |

FOREIGN PATENT DOCUMENTS

| | | | | |
|---|---|---|---|---|
| EP | 0 524 836 A | 1/1993 | | |
| EP | 0921133 A1 | 6/1999 | | |
| FR | 1 149 536 A | 12/1957 | | |
| GB | 785 631 | 10/1957 | | |
| GB | 1 220 384 A | 1/1971 | | |
| GB | 1365253 | 8/1974 | | |
| GB | 1 480 112 | 7/1977 | | |
| GB | 2 137 627 | 10/1984 | | |
| GB | 0486183 A1 | * 5/1992 | | C08J/5/02 |
| JP | 59199701 | 11/1984 | | |
| JP | 60-197713 | 10/1985 | | |
| JP | 5186902 | 7/1993 | | |
| JP | 6048066 | 2/1994 | | |
| JP | 6340758 | 12/1994 | | |
| JP | 19819/1995 | 5/1995 | | |
| JP | 8072170 | 3/1996 | | |

* cited by examiner

NON-ADHESIVE LATEX PRODUCTS

This application is a Continuation-in-Part (CIP) of and claims the benefit of priority under 35 USC §120 of international application no. PCT/JP00/03370, filed on May 25, 2000, which claims the benefit of priority of Japanese patent application serial no. 2000-121767, filed March 18, 2000 and Japanese patent application serial no. 1999-149718, filed May 28, 1999. The aforementioned applications are explicitly incorporated herein by reference in their entirety and for all purposes.

TECHNICAL FIELD

The present invention relates to a novel non-adhesive carboxylated latex product and to a novel process for manufacturing the same. Further, the present invention provides a latex product with high durability.

BACKGROUND

Carboxylated latex products include dipped products such as balloons, gloves, fingerstalls and condoms; extruded products such as rubber threads and rubber pipes; cast-molded products such as balloons and toys; and whole rubber products and products having rubber surfaces such as rubber sheets, hoses and draw cloths. Carboxylated latex products are apt to have adhesive surfaces which can negatively affect the manufacturing of the products or produce defective articles. Further, they are not ideal for producing products having a desired shape such as non-adhesive rolled fingerstalls.

Heretofore, to overcome these defects, adhesion preventing agents have been used. Adhesion preventing agents have generally been powdered substances called dusting powder (or simply powder). The powder is generally mica, talc, calcium carbonate, white carbon or corn starch. The powder, however, can spread to articles in contact with the latex product and become the cause of various problems if the article is a precision instrument. Also, the appearance of the latex product is damaged. In July 1999, the FDA issued a regulation on medical rubber gloves stating that the powder quantity on synthetic rubber medical gloves should be 120 mg or less per glove. For natural rubber medical gloves, the regulation stated that the soluble protein be 1200 $\mu$g per glove or less to prevent the latex allergy resulting from the proteins. A shift from natural rubber gloves to synthetic rubber gloves is anticipated. Thus, making synthetic rubber products non-adhesive is an important technical issue to be solved.

The general method of adhesion prevention, other than the use of powder, includes halogenation by post-chlorination treatment. For example, U.S. Pat. Nos. 3,411,982 and 3,740,262 disclose that halogenation makes the surface of rubber gloves slippery. U.S. Pat. No. 4,304,008 discloses halogenation, in place of powder, facilitates donning rubber products. U.S. Pat. No. 3,740,262 discloses halogenating gloves where the outside surface is powder-free and the inside surface is powdered.

Halogenation is a method in which a thin layer of halogenated rubber is formed on the product surface to prevent adhesion and blooming. This method is fairly widely used, providing a rubber product having a clean surface free of powder. However, when the degree of halogenation is too high, discoloration can occur, the surface can become brittle and cause cracks, or heat resistance can deteriorate. Further, there is the danger that any contacting metal may be corroded. Above all things, many users hesitate to use such products because of their negative environmental impact.

U.S. Pat. No. 4,304,008 discloses surgical gloves wherein the inside layer comprises a natural rubber and the outside layer a halogen-resistant silicone. The inside layer is halogenated to give a non-adhesive property.

The deficiencies of halogenation are set forth in U.S. Pat. No. 5,284,607. In the patent, medical gloves are formed using an acid-soluble powder, which is then dissolved by treating with an acid such as nitric acid. Thereafter, the gloves are chlorinated by a bleaching agent.

There are a variety of improvements in the methods for manufacturing rubber products, which use powders or substances having particulate structures.

U.S. Pat. No. 4,070,713 discloses medical gloves comprising two layers, i.e., outside and inside layers, of elastic substances. In the inside layer, a particulate substance such as zinc oxide or titanium oxide is firmly embedded and partially exposed to come in contact with the skin.

U.S. Pat. No. 4,143,109 discloses a manufacturing method related to the above-mentioned patent.

U.S. Pat. No. 5,138,719 discloses a method for making powder-free gloves, fingerstalls and the like from latex and microcapsules. The microcapsules are disersed and distributed in the latex so that their concentration may increase from the outside surface of the product toward the inside surface thereof, to build a concentration gradient. The microcapsule concentration is high on the inside surface, and this gives a good lubricious property and ease in donning without the use of powder.

U.S. Pat. No. 5,881,386 discloses gloves having two layers, with the two layers comprising polyvinyl chloride and polyesterpolyurethane. The inside polyesterpolyurethane layer is incorporated with a particulate substance of 1 to 75 $\mu$m.

Japanese Patent Application Laid-Open (Kokai) No.11-12823 discloses a technology for manufacturing working gloves with improved dusting properties by dipping the inside surface in a treating agent containing a powder of 0.1 to 1.5 $\mu$m followed by drying. The working gloves, used for clean rooms, are manufactured from polyvinylidene chloride paste sol.

Japanese Patent Application Laid-Open (Kokai) No.11-61527 discloses rubber gloves excellent for donning and doffing, which have a slippery resin layer, having been dipped in an aqueous dispersing liquid containing a synthetic rubber latex that is not coagulated by a coagulant contained in the gloves themselves, and containing an organic filler.

Japanese Patent Application Laid-Open (Kohyo) No.9-501983 discloses a water-dispersible silicone modified dispersion powder composition and a method of manufacturing it, and describes that the composition can be used as an antiblocking agent.

In recent years, products have been developed with various substances coated on the surface of latex products.

U.S. Pat. No. 4,310,928 provides surgery gloves by dispersing an oil and fat or lipophilic substance in a coagulation liquid and coating it on the surface of natural rubber. To prevent separation of the oil and fat or lipophilic substance, a surface active agent is added to the coagulation liquid.

U.S. Pat. Nos. 5,780,112 and 5,974,589 disclose a method of attaching a high density straight-chain hydrocarbon polymer, in particular polyethylene, to the surface of a natural rubber by chlorine generated by acidifying a hypochlorite. The latex product thus treated is non-adhesive without the use of powder.

Japanese Patent Application Laid-Open (Kohyo) No.11-507085 discloses a flexible copolymer coating which can be bonded firmly to the surface of a rubber article and extend, without separation, from the bonded surface. The patent, taking into consideration the need to remove the latex product from the dipping former and dry and wet wearing conditions, discloses an emulsion type copolymer between a reactive, low surface energy monomer, preferably a silicone oligomer, and an alkyl acrylate and a reactive hard monomer.

There are many disclosures on the methods for preparing powder-free gloves by coating a hydrophilic hydrogel forming polymer on the rubber surface and curing the polymer layer. Examples include U.S. Pat. Nos. 3,326,742; 3,585,103; 3,607,473; 3,745,042; 3,901,755; 3,925,138; 3,930,076; 3,940,533; 3,966,530; 4,024,317; 4,110,495; and 4,125,477.

Further, U.S. Pat. No. 4,499,154 discloses a method of manufacturing a talc-free product by immersing a dipping former in a natural rubber latex, leaching the product in hot water, impregnating the product with a dilute acid, neutralizing the surface with water or an aqueous alkali solution, dipping in a hydrophilic hydrogel formable polymer such as a copolymer of 2-hydroxyethylmethacrylate and methacrylic acid or 2-ethylhexylacrylate and a crosslinking agent thereof, heating the polymer layer to fix it to the rubber, vulcanizing the rubber, removing the product from the dipping former, coating it with a silicone containing a surfactant, and providing heat. This method also discloses that the lubricious property for wet hands is improved by crosslinking the layer of the hydrogel polymer of the invention and, thereafter, treating it with a cationic surfactant such as a long chain aliphatic amine. The patent also discloses that impregnating the rubber surface with an aluminum salt after acid treatment is preferable. This method can produce powder-free rubber products, but it includes many steps and raises the manufacturing costs excessively. Moreover, it cannot be used for products, which should not include silicone.

U.S. Pat. No. 4,575,476 discloses that the coat layer of a specific 2-oxyethyl methacrylate hydrogel polymer that has a good lubricious property for use with dry hands. Further, by treating the above-mentioned hydrogel layer with a surfactant, in particular with a cationic surfactant and a long chain aliphatic amine, the lubricious property for use with wet hands is improved.

Furthermore, by treating the product with a silicone containing surfactant, the adhesiveness of the surface, without the hydrogel layer, is markedly improved.

U.S. Pat. No. 5,688,855 discloses that the hydrophilicity of a solid surface gives lubrication to the surface in the presence of water and that a hydrophilic concentration gradient is automatically generated within a coating by dissolving in one solvent a hydrogel forming polymer component and a water-soluble polymer component that has a low compatibility with the former component, coating them on the surface of a rubber product, and evaporating the solvent to cause phase separation of the two components.

Japanese Patent Application Laid-Open (Kokai) No.11-269708 discloses gloves laminated with a lubricant layer of a rubber or resin containing collagen on the inside surface of gloves provided with a base layer of a rubber or polymer.

One problem with coating the rubber surface is that layer separation can occur when the rubber is extended.

U.S. Pat. No. 4,499,154 discloses reinforcing the adhesion of a coating by undercoating an acid on the rubber surface.

W093/06996-A1 proposes using, as a coating, a polymer having a repeated structure of specific ether groups and ester groups.

U.S. Pat. No. 4,548,844 discloses improved adhesion between a rubber layer and a hydrogel layer through acid treatment. It also discloses that, by undercoating an aluminum cation or a cation of trivalence or more, prior to the coating of the hydrogel polymer or by adding it to the hydrogel polymer, the adhesion of the rubber layer and the hydrogel polymer is enhanced. It is presumed that this is caused by a hydroxy or carboxyl group in the hydrogel polymer being bonded to a protein in the rubber latex.

Japanese Patent Application Laid-Open (Kokai) No.6-70942 discloses a multilayer product comprising a first layer formed from a natural rubber, a second layer of a natural rubber, polyurethane, poly(acrylamide/acrylic acid) and polyethylene oxide, and a third layer of an acryl copolymer and fluorocarbon telomer resin. The product can be donned under dry or wet conditions without the use of powder.

Japanese Patent Application Laid-Open (Kokai) No.10-95867 discloses production of powder-free medical gloves by coating a lubricating composition comprising a first and second composition on the surface of an elastomeric product on the wearer's side, the inside. The first composition comprises at least one compound selected from the group consisting of acetylene diol, organosilicone, amino modified silicone, and cationic surfactant. The second composition is at least one compound selected from the group consisting of cationic surface active agent, organosilicone, amino-modified silicone and acetylene diol.

Japanese Patent Publication (Kokoku) No.7-4405 discloses a method of treating a surface with a modified polysiloxane.

The methods for manufacturing rubber products containing no dusting powder include a method in which a bivalent coagulant metal salt, such as calcium nitrate, and a latex stabilized by adding a water soluble surfactant stable against the metal salt, preferably a nonionic surfactant or a resin polymer, are brought into co-existence in a coagulation liquid. A dipping former, coated with the coagulant, is dipped in the latex to coat one side of the rubber product. Although this method fails to make the rubber product substantially non-adhesive, it is possible to make the rubber product non-adhesive by adding a peeling or anti-adhesion agent to the coagulant composition as a third component.

U.S. Pat. Nos. 3,286,011 and 3,411,982 to Kavalir et al. disclose the above-mentioned technology. The patents, however, fail to make the product powder-free because it uses powder as the peeling agent.

The patents disclose that polyvalent metal salts like calcium, magnesium and aluminum can be used as the latex coagulants.

The above-mentioned U.S. Pat. No. 4,310,928 discloses a method of fabricating surgery gloves, which can be removed from a dipping former by dispersing a lipophilic substance into the coagulant liquid, such as calcium nitrate.

Japanese Patent Application Laid-Open (Kohyo) No. 10-508899 discloses a method for producing a rubber article free of powder by adding to the coagulant an acrylic emulsion copolymer coating composition and a silicone emulsion. The coating composition is made by copolymerization of a reactive silicone acrylate, an alkyl acrylate and a hard monomer, but such a composition is a known substance. The patent clarifies that the release becomes easy only when the silicone emulsion is added to the composition and that the gloves performs well under dry-type conditions.

EP 640,623 discloses a coagulant for natural rubber comprising a salt-stable polychloroprene or polyurethane and a bivalent metal salt. Powder-free rubber gloves can be manufactured by further adding to the coagulant a peeling agent consisting of a polyethylene wax emulsion and a cationic surfactant.

In Japanese Patent Application Laid-Open (Kokai) No.11-236466, surfactants and various waxes such as polypropylene wax emulsion, instead of a polyethylene wax emulsion, were employed as an adhesion eliminating agent or releasing agent. The cationic surfactant functions to stabilize the polychloroprene added to the coagulant and functions as a releasing agent between the polychloroprene and the dipping former, having a greater affinity for the dipping former than the pertinent polymer.

Japanese Patent Publication (Kokoku) No.2-42082 discloses a coagulant composition formed by adding a latex and a surfactant or bivalent or trivalent metal salt into water.

In Japanese Patent Application Laid-Open (Kohyo) No.9-511708, the Teague method is used in the manufacture of polyurethane coated gloves. Namely, a first layer is formed by dipping a former in an aqueous dispersion liquid or emulsion of a polyurethane polymer or copolymer. The first layer is dipped in a coagulant then a latex compound to form a second layer. This application also discloses a method of forming a lubricating polymer layer over the second layer.

There is disclosed technology for making two powder-free gloves which use novel raw materials.

U.S. Pat. No. 5,851,683 proposes a special successive copolymerization polymer to make powder-free gloves comprising a thermoplastic elastomer for use in clean rooms.

Methods of preventing the adhesion of emulsion/latex products are important to both manufacturing and use of the products. Although various proposals have been advanced, many of these technologies are considerably complicated. A method that is simple, effective and economical has not been developed. One reason for this is that the main material is a natural rubber latex with a strong adhesive property with complicated causes for creating adhesion. Due to this, the treatment materials and techniques for preventing adhesion can be complex.

The present invention, taking into consideration the above-mentioned current status of adhesion treating technology, provides novel powder-free, non-adhesive carboxylated latex products and novel methods of manufacturing the same. Further, the present invention provides latex products having excellent durability without sulfur vulcanization.

DISCLOSURE OF THE INVENTION

In our intense study to solve the above-mentioned problems, we discovered that the adhesiveness of the surface of the latex product is strong if the surface of a carboxylated latex product is not sufficiently crosslinked with a bivalent metal compound as a coagulant. Furthermore, if sufficient crosslinking is conducted with a mono- or bi-valent metal compound, the resulting non-adhesion is insufficient since heating can cause adhesion between the surfaces of latex products. Assuming that the cause of the adhesion of a carboxylated latex product may lie in that the carboxyl group of the latex forms a hydrogen bond through water, we studied methods to inhibit this hydrogen bond formation.

We first studied use of a metal compound having tri- or more valence as an external crosslinking agent. For example, aluminum salt, a representative trivalent metal cation, possesses a very strong coagulating ability according to the Shultz-Hardy Law. But, when only aluminum compound is used as the external coagulant for the purpose of making a dipped product, only an extremely thin film is formed. However, we found that a film having an acceptable thickness can be formed by forming a layer of an external crosslinking agent of aluminum compound on a dipping former, followed by a coagulant layer of the normally used mono- or bi-valent metal salt, then dipping it into the latex solution. In this procedure, the aluminum compound crosslinking layer is formed in the innermost layer. Surprisingly, it was found that the inside surface of the dipped product crosslinked with the aluminum compound is non-adhesive and that bringing each of the inside surfaces into close contact followed by heating under wet conditions does not cause them to adhere to each other.

On the other hand, when the external crosslinking agent layer of the aluminum compound is formed on the external coagulant layer of mono- or bi-valent metal salt and subsequently dipped into the latex solution, only a thin film is formed. However, when external crosslinking agent layer is formed on the external coagulant layer comprising a mixture of the mono- or bi-valent metal salt and the aluminum compound followed by dipping in the latex solution, surprisingly a film having the normal thickness and a non-adhesive inside surface is formed.

Next, we studied making the outside surface of the dipped product non-adhesive. A film was shaped by forming the external coagulant layer on the dipping former and dipping it into the latex. The film was further dipped into the aluminum compound solution according to the usual method, followed by heating, thereby forming an aluminum compound crosslinking layer on the outside surface of the film. The outside surface of the film was non-adhesive. Further, after releasing the dipped product from the dipping former, both surfaces were dipped in the aluminum compound solution and subjected to subsequent heating. Both surfaces were found to be non-adhesive.

Based on the above-mentioned findings, the crosslinking layer formation reaction of the latex surface was tested using various compounds of metal elements having three or more valences. It was found that they could be used to produce a latex article having a non-adhesive surface.

Furthermore, we tested treating the surface of the latex base substance with various organic crosslinking agents that crosslink the carboxy group of the carboxylated latex in the same manner as the metal compounds having three or more valences. The results, showed that the organic crosslinking agents produced non-adhesive latex products as did the tri- or more valent metal compounds. Emulsion type crosslinking agents tended to have a large effect, while water soluble organic crosslinking agents showed less of an effect. This held true even when the cross linking agents were of the same type. Moreover, the latex film formed by the dipping method using the water-soluble crosslinking agent added to the coagulant raised problems in that cracks developed and the film strength was poor, to name a few. Presumably, the crosslinking agent diffused into the inside of the film to cause over-vulcanization, which brought forth the deterioration in the strength of the film.

We added chemicals having a coagulating effect to the emulsion latex in order to prevent the diffusion of the crosslinking agent and confirmed that the internally added inorganic aluminum crosslinking agents such as aluminates and aluminum hydroxide gels (also referred to herein as "aluminum type inorganic crosslinking agents") could be added to the emulsion latex without coagulating the carboxylated latex. In addition, the latex film that was not made non-adhesive in the treatment with a concentration as high as 1% of a water-soluble crosslinking agent such as oxazoline crosslinking agent, e.g. Epocross W (made by Nippon Shokubai), was made non-adhesive when a compound having a coagulating effect was added even in a concentration as extremely low as 10 ppm. As used herein, "external," when used in conjunction with a compound, refers to the fact that the compound is not added to the latex. "Internal" refers to the fact that the compound is added or incorporated into the latex. The effect of the diffusion of organic crosslinking agents when an internally added aluminum type inorganic crosslinking agent, such as aluminate or aluminum hydroxide get, is added to an emulsion latex was studied. After forming a film with the coagulant containing organic crosslinking agent, the effect on the film strength based on the temperature at the leaching stage was examined. The film strength decreased at the usual leaching stage temperature of 50 to 60° C., but a decrease in film strength was not observed when the treatment at the leaching stage was conducted at 70° C. or more. Presumably, unlike the tri- or more valent metal compounds in the coagulation liquid, the crosslinking agent in the aqueous treatment solution, being poorly reactive with the carboxyl group in the latex at a low temperature, diffuses toward the Z-axis direction and does not stay on the surface of the latex product, causing a deterioration in film strength.

The effect of decreasing the concentration of the organic crosslinking agent on the adhesion and strength of the latex product was examined. Even with a concentration of the organic crosslinking agent as extremely low as 0.001% ($2 \times 10^{-4}$ part per latex solids), the latex product showed non-adhesion and the strength of the product was equivalent to that of the untreated product. The effect of the organic crosslinking agents on the strength differs according to the properties of the crosslinking agent. Those which have a lower degree of diffusion in the Z-axis direction, or those that react immediately on the surface of the latex and do not diffuse internally, exert less influence on the product strength.

We conducted a durability test for fingerstalls. A fingerstall obtained by vulcanizing the carboxylated latex with zinc oxide, although showing good results in the strength test, was found to be very poor in durability since the film developed cracks in several hours to one day of wear. This is because the defect of ion crosslinking comes to the forefront on the surface of the fingerstalls.

We conducted a durability test for the above-mentioned fingerstalls, which were obtained by adding an internally added aluminum type inorganic crosslinking agent such as aluminate or aluminum hydroxide gel to an emulsion latex. Unexpectedly, they did not tear when worn for a period from one day to one week. This is thought to be because, when the ion crosslinking by zinc oxide is cleaved upon use, the aluminum ion retaining crosslinking power repairs the cleaved points. Thus, by adding the internally added aluminum type inorganic crosslinking agent such as aluminate or aluminum hydroxide gel into the carboxylated latex, a non-adhesive treatment becomes possible even with an extremely low concentration of the organic crosslinking agent that hitherto has been incapable of use in non-adhesion treatments. Further, it becomes possible to produce latex products excellent in durability without sulfur vulcanization.

Tests on tri- or more valent metal compound crosslinking agents gave similar results.

Other organic crosslinking agents for carboxyl groups can make the carboxylated latex product non-adhesive at a lower concentration, as in oxazoline type crosslinking agents.

Organic compounds, which are not crosslinking agents for carboxyl groups but are considered to react with carboxyl groups, have similar effects. Such compounds include glyoxal, polyamide compound, polyamide polyurea compound, polyamide polyureaglyoxal condensation reaction product, polyamine polyurea compound, polyamideamine polyurea compound, polyamideamine compound, polyamideamine epihalohydrine condensation reaction product, polyamideamine formaldehyde condensation reaction product, polyamine epihalohydrine condensation reaction product, polyamine formaldehyde condensation reaction product, polyamide polturea epihalohydrine condensation reaction product, polyamide polyurea formaldehyde condensation reaction product, polyamine polyurea epihalohydrine condensation reaction product, polyamine polyurea formaldehyde condensation reaction product, polyamideamine polyurea epihalohydrine condensation reaction product, and polyamideamine polyurea formaldehyde condensation reaction product. These compounds have been developed as waterproof endowing agent, sizing agent, printability improver, wet strength enhancing agent, and paper strength reinforcing agent of papers, and share the trait that they are all chemicals for controlling hydrogen bonds in paper.

Next, we studied compounds such as monofunctional epoxy compounds and monofunctional amines that do not crosslink with the carboxyl group of the latex, but that react with the carboxyl group to inhibit the formation of hydrogen bond derived from the carboxyl group.

As a result, it was confirmed that these compounds, which are considered to bond to a carboxyl group leading to hydrophobicity, afford similar effects to those of the beforementioned compounds.

We studied sizing agents, which are used in the field of paper as chemicals to block carboxyl groups. The typical example of a sizing agent is the rosin type. The main ingredient of rosin is abietic acid. Rosin coats pulp fibers and exhibits excellent hydrophobicity. The contact angle of rosin and water can be as large as 53°. If aluminum is bonded, the contact angle becomes as extremely large as 130°. Thus, rosin is a hydrophobicity endowing agent. The rosin sizing agent was tested in the same manner as the above-mentioned compounds, and its effect as a blocking agent of carboxyl group was confirmed. This effect of the sizing agent may be because it coats the latex surface physico-chemically or physically into hydrophobicity. It is theorized that aluminum ion plays a big role in this action.

Further, in recent years, alkylketenedimer(AKD), alkenylsuccinic acid anhydride(ASA), cationic sizing agent, and the like have been used as sizing agents for neutral paper. These neutral sizing agents also had a similar effect on non-adhesiveness. Regarding the hydrophobicity effect of AKD and ASA, it is generally believed that they create hydrophobicity by chemically bonding to a hydrophilic group. But, there is a view that they cause autolysis on the surface of fibers to lose hydrophilicity and the whole compound becomes hydrophobic. Thus, the hydrophilic group works as anchor. In any event, it is evident that the relevant sizing agent blocks the carboxyl group on the latex surface chemically, physico-chemically or physically to generate hydrophobicity of the surface.

We also studied making the surface of latex products hydrophobic chemically or physically, taking the above-mentioned hydrophobicity effect into consideration. First, we looked to the hydrophobic group of surfactants and examined nonionic surfactants. As a result, it was found that HLB, an index of hydrophilicity and hydrophobicity, could not interpret the degree of non-adhesion. Further, cationic and amphoteric surfactants do not have such an index. We thought it convenient to determine the propriety by conducting adhesion test 1 or 2 as shown in the below-mentioned examples. The surfactant that showed a non-adhesive effect is called hereinafter a non-adhesive surfactant.

The anionic surfactant has an effect similar to the cationic and amphoteric surfactants. However, the anionic surfactant loses the function of a surfactant as soon as it forms a metal soap with polyvalent metal salts derived from a coagulant. Many of the metal salts of the anionic surfactants have adhesiveness, and the treatment with an anionic surfactant sometimes produces an adverse effect. To grasp the characteristics of the compound itself, it is necessary to conduct the adhesion test.

For the surfactant to exhibit the non-adhesive effect, it is necessary to add an internally added aluminum type inorganic crosslinking agent such as aluminate or hydroxyaluminum gel directly into an emulsion latex.

We further studied, based on the above-mentioned findings, a method of directly adding a carboxyl-group blocking agent into a carboxylated latex. When an article is made by the dipping method, the latex film, after the dipping, is extracted with hot water at the leaching stage. Accordingly, the carboxyl-group blocking agent incorporated in the latex leaches out at the leaching stage, failing to make the carboxylated latex product non-adhesive. On the other hand, when the carboxyl-group blocking agent is an emulsion type, when it reacts with a carboxylated emulsion latex, or when it is adsorbed on a carboxylated emulsion latex, it reacts with a bivalent metal salt, preferably calcium salt, in the coagulant and it does not leach out. In cases where there is a special condition such that the carboxyl group blocking agent does not leach out, incorporating the carboxyl-group blocking agent into the carboxylated emulsion latex gives a non-adhesive product. Example of a special condition includes a condition that the calcium soap formed above has a non-adhesive effect or a condition that the carboxyl-group blocking agent does not leach out by reacting with the aluminum type inorganic crosslinking agent such as aluminate or aluminumhydroxide gel added in the carboxylated emulsion latex.

We also studied techniques for making carboxylated latex products non-adhesive through chlorination. Chlorination, wherein chlorine adds to the double bonds of rubber molecules on both surfaces, outside and inside, of carboxylated latex products, produces, a layer of chlorinated hydrocarbon, though it raises environmental concerns.

For this reason, both surfaces of the rubber products lose their rubbery properties, leading to the hydrophobic and non-adhesive surfaces. There are many problems in manufacturing, which are affected by the quality of chlorination. A big problem in the manufacturing process is that on-machine chlorination of both sides is not possible, since one side of the article to be chlorinated is attached to the former. Usually, chlorination is conducted as a separate step after the product has been removed from the former after on-machine chlorination of only the outside surface with the product removed from the former and with its inside surface reversed outwardly. This step reduces production efficiency.

We have found the problem can be solved by a method wherein non-adhesion of the outside surface is carried out by on-machine chlorination and non-adhesion of the inside surface is carried out by adopting a non-adhesion providing technique separately invented by us (JP Application No. 2000-139733).

The techniques for providing non-adhesion to carboxylated latex products have been mentioned above. By chlorinating the outside surface of the carboxylated latex products, which had been manufactured by using such techniques, it was possible to produce non-adhesive carboxylated latex products. In cases where the products are rubber gloves, they are turn inside out when they are removed from the former. Consequently, the inside surface has been subjected to chlorination, and gloves that are good in donning and doffing are fabricated.

The carboxylated latex film, which has been subjected to non-adhesion measures as to the inside surface, can be on-machine chlorinated by being dipped into a chlorine aqueous solution or by contacting the outside surface with chlorine gas. The outside surface of the chlorinated carboxylated latex products is then non-adhesive, and the inside surface thereof is non-adhesive through the non-adhesion providing treatment provided herein.

Further, in the case of gloves, they are turned inside out when they are peeled off from the former, and the inside surface corresponds to the surface that has undergone the chlorination. For this reason, donning and doffing the gloves are easy. As used herein, the outside surface in the present invention is the surface that is not in contact with the former in the dipping process, and the inside surface is the one that is in contact with the former.

Chlorination of the outside surface can be effected by any known method. That is, methods can be adopted in which a formed carboxylated latex film is dipped in a chlorine aqueous solution or put into direct contact with chlorine gas. Since only one side is to be chlorinated, it can be performed by on-machine means.

As mentioned above, it is possible by using the present invention to fabricate the latex product, which is non-adhesive in one or both surfaces thereof. The surfaces of such products do not adhere together even when one surface comes in contact with the other under heat during and after manufacturing. Accordingly, products are provided that have not existed until now.

One such product is a non-adhesive fingerstall mechanically wound on-machine before removing from the dipping former. A fingerstall wound upon itself is known, and its usefulness has been recognized because of its ease of use. However, both surfaces of the fingerstall, a latex product, are intrinsically adhesive, and in order to manufacture the wound product, the fingerstall had to be made non-adhesive by a treatment such as powdering and post-chlorination, followed by winding with human hands. This made it impossible to maintain the cleanliness of the product, which would affect its ability to be used in a workplace, such as a clean room, where precisely processed articles are manufactured. In contrast, the present invention, which is able to make both surfaces of a formed latex non-adhesive, can provide a method for mechanically winding (rolling) a fingerstall on a dipping former and can, thus, maintain the cleanliness of the product to a high degree.

Recently, thin fingerstalls are desired since wearing thick ones tend to cause exhaustion. The thinner the fingerstall, however, the more difficult it is to don. Therefore, what is desired is an easy to don wound fingerstall that is thin, powder-free, non-adhesive and clean. By utilizing the property that both surfaces of the fingerstall are non-adhesive, a fingerstall with a rolled lip can easily be manufactured. In manufacturing the fingerstall, the top of the stall can be left adhesive by not providing it a layer of carboxyl-group blocking agent, thus, the whole fingerstall can be wound up, and then unwound. By this, the adhesive portion remains as the rolled lip.

Hitherto, the rolled lip was formed first by winding up only the top of the stall to make the rolled lip, and, thereafter, the stall was released from the former in another step. The rolled lip facilitates donning and doffing of the stall and is highly desired for flat products. Further, after formation of the rolled lip by the conventional method, a non-adhesion treatment may be conducted. This procedure is also applicable to the wound fingerstall described in the preceding paragraph, thereby providing the fingerstall with a rolled lip.

The present invention relates to:

(1) A non-adhesive carboxylated latex product incorporated with a carboxyl-group blocking agent;

(2) A non-adhesive carboxylated latex product having a layer treated with a carboxyl-group blocking agent on one or both surfaces of a carboxylated latex product or a carboxylated latex product incorporated with a carboxyl group blocking agent;

(3) A non-adhesive carboxylated latex product having a layer treated with a carboxyl group blocking agent on the inside surface of a carboxylated latex product or a carboxylated latex product incorporated with a carboxyl group blocking agent and having a chlorination treatment on the outside surface; . (4) A non-adhesive carboxylated latex product according to (1) to (3), wherein the carboxylated latex is acrylonitrile—butadiene rubber (NBR), styrene—butadiene rubber (SBR), chloroprene—rubber (CR), or methyl methacrylate—butadiene rubber (MBR);

(5) A durable, non-adhesive carboxylated latex product according to (1) to (4), wherein the carboxylated latex is added and crosslinked with an internally added aluminum-type inorganic crosslinking agent;

(6) A non-adhesive carboxylated latex product according to (1) to (5), wherein the latex product is a dipped product;

(7) A non-adhesive carboxylated latex product according to (6), wherein the dipped product is a fingerstall, glove, balloon or condom;

(8) A non-adhesive carboxylated latex product according to (1) to (7), wherein the carboxyl-group blocking agent is a metal element crosslinking agent having three or more valences;

(9) A non-adhesive carboxylated latex product according to (8), wherein the metal element crosslinking agent having three or more valences includes at least one compound selected from aluminum, titanium or zirconium compounds;

(10) A non-adhesive carboxylated latex product according to (1) to (7), wherein the carboxyl-group blocking agent is an organic crosslinking agent for the carboxyl group of the carboxylated latex;

(11) A non-adhesive carboxylated latex product according to (10), wherein the organic crosslinking agent for the carboxyl group includes at least one compound selected from aziridine compounds, epoxy compounds, blocked isocyanates, oxazoline compounds, carbodiimido compounds, melamineformaldehyde resins, ureaformaldehyde resins, isocyanates, phenolformaldehyde resins, glycols, polyols, diamines, polyamines, hexamethoxymethylmelamines and methylolacrylamides;

(12) A non-adhesive carboxylated latex product according to (1) to (7), wherein the carboxyl-group blocking agent includes at least one compound selected from glyoxals, polyamide compounds, polyamide polyurea compounds, polyamine polyurea compounds, polyamideamine polyurea compounds, polyamide polyurea glyoxal reaction products, polyamideamine compounds, polyamideamine epihalohydrine condensation reaction products, polyamideamine formaldehyde condensation reaction products, polyamine epihalohydrine condensation reaction products, polyamine formaldehyde condensation reaction products, polyamide polyurea epihalohydrine condensation reaction products, polyamide polyurea formaldehyde condensation reaction products, polyamine polyurea epihalohydrine condensation reaction products, polyamine polyurea formaldehyde condensation reaction products, polyamideamine polyurea epihalohydrine condensation reaction products, and polyamideamine polyurea formaldehyde condensation reaction products;

(13) A non-adhesive carboxylated latex product according to (1) to (7), wherein the carboxyl-group blocking agent includes at least one compound selected from monofunctional amines, monofunctional epoxy compounds, monofunctional isocyanates and mono functional blocked isocyanates;

(14) A non-adhesive carboxylated latex product according to (1) to (7), wherein the carboxyl-group blocking agent is a sizing agent;

(15) A non-adhesive carboxylated latex product according to (1) to (7), wherein the carboxyl-group blocking agent is a non-adhesion surfactant;

(16) A method for producing a non-adhesive carboxylated latex product according to (1) to (15), wherein one or both surfaces of the latex product are brought into contact with one or more of the carboxyl-group blocking agent solutions described in (8) to (15) to attach the carboxyl-group blocking agent to the latex surface;

(17) A method for producing a non-adhesive carboxylated latex dipped product, characterized in that there is used a solution of a mono- or bi-valent external coagulant for carboxylated latex which is mixed with or dissolved in one or more of the carboxyl group blocking agents described in (8) to (15);

(18) A method for producing a non-adhesive carboxylated latex dipped product, characterized in that a dipping former is dipped and deposited with one or more of the carboxyl-group blocking agent described in (8) to (15), dipped and deposited with a mono- or bi-valent external coagulant, and then dipped in a latex;

(19) A method for producing a non-adhesive carboxylated latex dipped product, characterized in that a dipping former is dipped and deposited with one or more of the carboxyl-group blocking agents described (8) to (1 5), then dipped in a latex liquid to form a latex film, further dipped in a mono- or bi-valent external coagulant solution, and subsequently dipped in the carboxylated latex again;

(20) A method for producing a non-adhesive carboxylated latex dipped product, characterized in that a dipping former is dipped in a mixture of one or more of the carboxyl-group blocking agents described in (8) to (15) and a carboxylated latex stable to the blocking agent to form a latex film, further dipped in a mono- or bi-valent external coagulant solution, and, thereafter, dipped in the carboxylated latex again;

(21) A method for producing a non-adhesive carboxylated latex dipped product, characterized in that a dipping former is dipped in a mono- or bi-valent coagulant suspension for carboxylated latex which contains, as the carrier, fine powder of one or more of the carboxyl group blocking agents described in (8) to (15) that is hardly soluble or insoluble in water or alcohol, and subsequently dipped in the carboxylated latex liquid;

(22) A non-adhesive fingerstall, wherein the fingerstall described in (7) has a shape mechanically wound from the mouth before being removed from the dipping former;

(23) A non-adhesive fingerstall according to (7) or (22) which has a rolled lip;

(24) A method for producing a non-adhesive fingerstall with a rolled lip according to (23), characterized in that an adhesive portion is provided on the upper part at the time of dipping and then wound; and

(25) A method for producing a non-adhesive fingerstall according to (7) or (22), characterized in that the outside surface is treated with a carboxyl group blocking agent after a rolled lip is provided.

The term carboxyl group blocking agent as used herein means a substance which blocks a carboxyl group chemically, physico-chemically or physically and inhibits the formation of a hydrogen bond derived from the carboxyl group. Specifically, it means a compound, which can make the carboxylated latex non-adhesive in the adhesion test 1 or 2 of the examples. Further, the non-adhesion surfactant refers to a surfactant, which can make the carboxylated latex non-adhesive in the adhesion test 1 or 2 of the examples.

DETAILED DESCRIPTION

Figure 1:
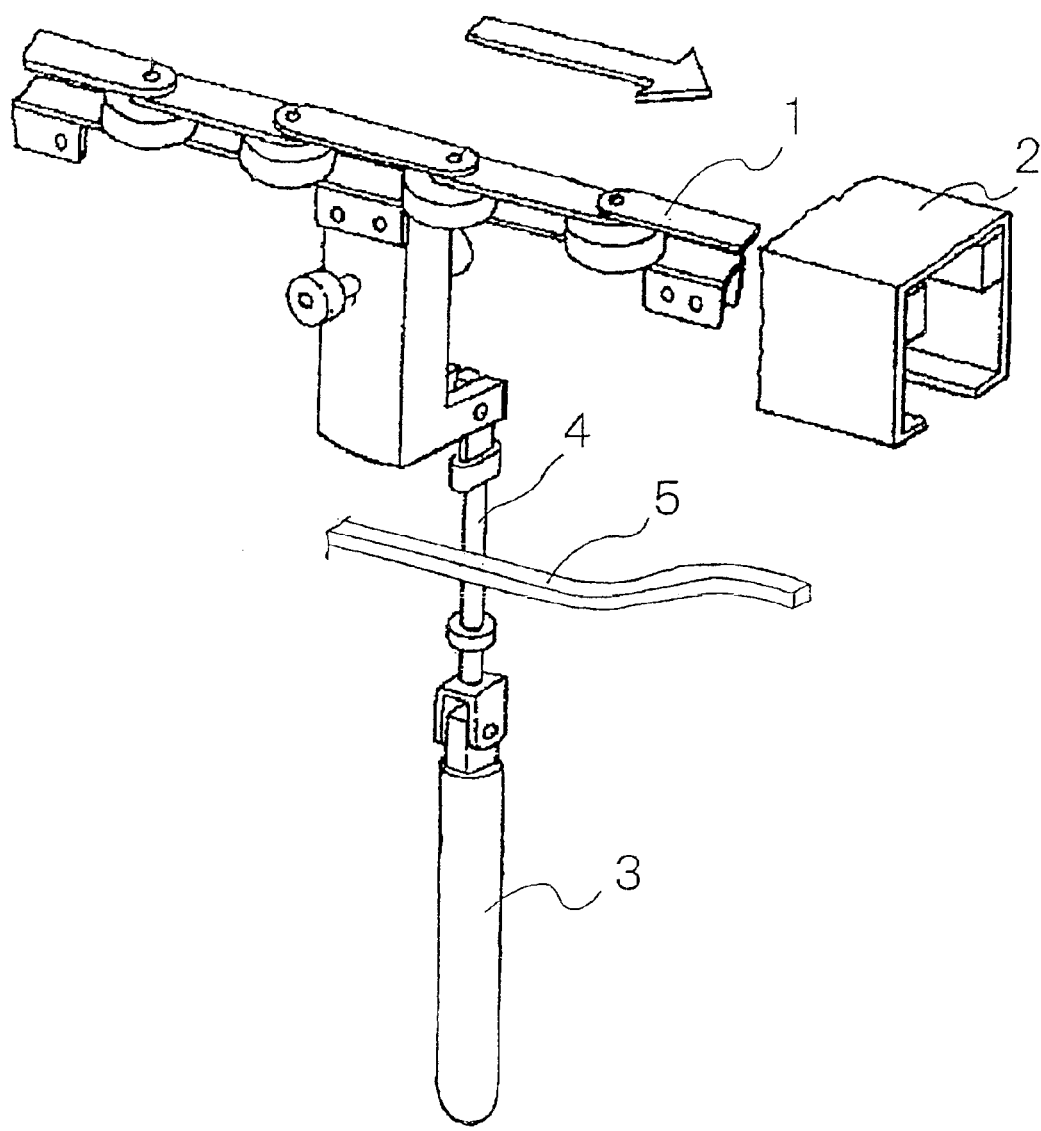
FIG. 1 is a perspective view of the dipping former transferring apparatus used in the examples. There is shown a chain 1, a guide rail 2, a dipping former 3, a rod 4, and a guide 5.

The present invention is described in more detail hereinafter.

The first non-adhesive carboxylated latex product of the invention is a latex product in which a non-adhesive property have been afforded to it by directly adding a carboxyl group blocking agent into an emulsion latex.

The second is a carboxylated latex product having a treatment layer of the carboxyl group blocking agent on one or both surfaces of the carboxylated latex base. Both products are intrinsically non-adhesive. If special use characteristics such as dry or wet wearing conditions are required, an outer polymer bonded layer can be provided further on the outside surface according to known technology. Latex products which require a non-adhesive treatment include, but are not limited to, dipped products such as balloons, gloves, fingerstalls and condoms, extruded products such as rubber threads and rubber pipes, cast-molded products such as balloons and toys, and whole rubber products or products having rubber surface such as rubber sheets, hoses and draw clothes.

The kind of carboxylated latex used herein is not limited, but among elastomer latexes of NBR, SBR, CR, MBR and the like, the ones subjected to carboxylation are preferable.

There is no limitation as to the vulcanizing agent to be added to the carboxylated latex. Regular vulcanizing agents can be used: e.g., agents for sulfur, peroxide, zinc oxide or radiation vulcanization. However, when the latex product is used in a field where the reaction of a metal and sulfur is undesirable, for example in the field of precision instruments, sulfur cannot be used as a vulcanizing agent.

For such use, a product vulcanized by zinc oxide is generally used, but there is a risk that it may break during wear because of ion crosslinking. Especially for thin gloves or fingerstalls, high durability is required. By adding an internally added aluminum type inorganic crosslinking agent into the carboxylated latex, durability is greatly improved. The range of compounds that can function as carboxyl group blocking agents can sharply increase, while the amount to be added can sharply decrease. Here, the internally added aluminum type inorganic crosslinking agent refers to an inorganic aluminum compound which does not coagulate the latex at ordinary temperatures even when directly added to the carboxylated latex and which crosslinks the carboxylated latex when heated. The typical examples, are alkali metal aluminates such as water-soluble sodium aluminate, alkaline earth metal aluminates such as sparingly soluble calcium aluminate, and aluminum hydroxide gel.

Also included are the groups of various aluminum compounds such as magnesium aluminate metasilicate, synthetic hydrotalcite, aluminosilicagel and aluminosilicate. In other words, they are compounds, which do not dissociate into aluminum ion when added, but combine with a carboxyl group of the latex through ionic crosslink when heated. The aluminum-ion crosslink of these compounds is considered to occur via aluminum hydroxide.

When the latex product is a dipped product, it is preferable to use an external coagulant, and any of the usually used external coagulants can be employed. Usually, mono- or bi-valent metal salts are used, and the monovalent salts include ammonium salts. Here, the external coagulant means one that is not directly incorporated into the latex but used in the coagulation- dipping process including deposition on the dipping former.

The carboxyl group blocking agent used in the invention is a compound which acts on a carboxyl group of the carboxylated latex chemically, physico-chemically or physically, thereby resulting in hydrophobicity which inhibits the formation of a hydrogen bond derived from the carboxyl group so as to make the latex product non-adhesive.

The first carboxyl group blocking agent is a tri-or more valent metal compound. Although any agent can be used if it has three or more valences, it is necessary to fully consider safety issues and side effects (discoloration) associated with the use of the compound.

Tri- or more valent metal compounds usable as the external crosslinking agent in the invention include ones which are soluble in water or alcohol and ones which are sparingly soluble or insoluble. The soluble trivalent metal compounds include aluminum salts, ferric salts, chromate and thorium salts. Particularly suitable are aluminum salts such as aluminum chloride, aluminum nitrate, aluminum sulfate and aluminum acetate.

Polyaluminumchloride_(PAC) and water-soluble polyaluminum hydroxide salt are preferable because they have three or more valences. Water-soluble polyaluminum_ hydroxide salt produces a non-adhesive effect at low concentrations comparable to that of organic crosslinking agents, as shown in the examples. If the metal is an amphoteric element, its metal acid salt is usable, sodium aluminate being a typical example. Observations suggest that sodium aluminate is converted into aluminum hydroxide on the film latex surface and causes crosslinking.

Metal compounds, sparingly soluble or insoluble in water or alcohol, that act as the external crosslinking agent include oxides, hydroxides and alkaline earth metal salts. Typical examples include aluminum hydroxide, calcium aluminate and magnesium aluminate. The aluminum compounds include various substances such as aluminosilicates, which fall within the scope of the invention. The usual crystalline aluminum hydroxide is hardly involved in the crosslinking reaction. The so-called amorphous aluminum hydroxide, when dispersed with a ball mill and made to have a large specific surface, is involved in the crosslinking reaction and is absorbed on the latex film surface formed. Further, calcium aluminate and magnesium aluminate are absorbed on the latex surface in the same way.

As used herein, the external crosslinking agent refers to one that is not directly incorporated into the base emulsion latex and crosslinks the latex by its contact with the surface of the emulsion latex or latex film.

The tetravalent metal compounds used in the invention include zirconium compounds such as zirconyl nitrate, ammonium, zirconyl carbonate zirconyl carbonate W, ammonium carbonate zirconuim oxychloride, and titanium compounds such as titanium lactate, titanium maleaic anhydride and titanium oxalate.

In the case of a tri- or more valent water soluble metal salt, the dissociated metal ion is cationic and reacts with the anion of carboxyl group even at low temperatures. Further, according to the Shultz-Hardy Law, it has a strong crosslinking force. Because of this, the diffusion of the metal ion having three or more valences is very weak, and the reduction in strength of the latex film is minimized. Accordingly, the quality of the final product remains good, even if the concentration of the metal salt is considerably high.

The tri- or more valent metal compounds used in the invention include organic compounds. Typical examples include carboxylic acid salts, such as the above-mentioned aluminum acetate, zirconium acetate, titanium lactate, titanium maleic anhydride, titanium oxalate and titanium lactate. Useful organic compounds are not limited to carboxylic acid salts.

The concentration of tri- or more valent metal external crosslinking agents varies depending on the kind of latex used, the amount of functional groups involved in the reaction, the kind and quantity of emulsifier or dispersant, the kind of crosslinking agent, treatment method, and the crosslinking agent's ability to coat the dipping former. Preferably, the concentration is in the range of 0.1 to 5% (of metal oxide corresponding to the metal element). When the agent is used by incorporating it into the external coagulant, it exhibits a sufficient effect at the concentration of 0.01 to 0.5%. In the cases where it is coated on the formed latex film and in the cases where the external coagulant layer is coated on the external crosslinking agent layer, a preferable concentration is 0.2 to 1%. When the agent is used by incorporating it into the external coagulant, it replaces monovalent cations of the latex, usually ammonium ion, potassium ion and sodium ion, to form a crosslink. When a coagulant having bivalent cations is used, the agent replaces the bivalent cation, usually calcium ion, to bond to the latex to form a crosslink.

In a system in which the internally added aluminum type inorganic crosslinking agent is directly added to the latex, the concentration of the external crosslinking agent can be decreased.

The second carboxyl group blocking agent is an organic crosslinking agent for the carboxyl group of the carboxylated emulsion latex. Any organic crosslinking agent is usable as long as it is capable of crosslinking a carboxyl group. Exemplary organic crosslinking agents include, but are not limited to, aziridine compound, epoxy compound, blocked isocyanate, oxazoline compound, carboimide compound, melamineformaldehyde resin, ureaformaldehyde resin, isocyanate, phenolformaldehyde resin, glycol, polyol, diamine, polyamine, hexamethoxymethylmelamine and methlolacrylamide. (See Newest Applied Technology of Latex Emulsion, page 323, Motoharu Okikura (ed) published by Chunichisha, Japan.)

The organic crosslinking agent for the carboxyl group reacts at a considerably high temperature. According to the invention, since the amount used is very small, it shows an effect at a temperature of about 90 to 120° C. However, if sufficient time lapses at a low temperature, the crosslinking agent diffuses in the Z-axis direction, and competes with the latex vulcanizer, such as zinc oxide, to restrain vulcanization, resulting in a decrease in film strength. Particularly, the temperature at the leaching stage of a dipping method is preferably 65° C. or more, for example 70° C. to 85° C. Temperatures of 85° C. or more are not preferable because bubbles can be generated between the dipping former and the film. When the concentration of organic crosslinking agent in the coagulant is high, diffusion of the crosslinking agent becomes greater and the strength is lowered. But, an emulsion type crosslinking agent or highly reactive crosslinking agent diffuses weakly, and the degree of the diffusion also differs depending on the solubility of the crosslinking agent in the coagulant solution. Therefore, it is preferable to determine optimal conditions through an adhesion test. A suitable concentration can be determined by carrying out the test at two levels of effective ingredient concentration, 0.025% and 0.0025%. The amount of crosslinking agent needed to make the carboxylated emulsion latex product non-adhesive is extremely small.

Organic compounds, which do not act as crosslinking agents for the carboxyl group but are thought to react with a carboxyl group, also have a similar effect. Examples of effective compounds include the following: glyoxal, polyamide compound, polyamidepolyurea compound, polyamidepolyureaglyoxal condensation reaction product, polyaminepolyurea compound, polyamideaminepolyurea compound, polyamideamine compound, polyamideamineepihalohydrine condensation reaction product, polyamideamineformaldehyde condensation product, polyamineepihalohydrine condensation reaction product, polyamineformaldehyde condensation reaction product, polyamidepolyureaepihalohydrine condensation reaction product, polyamidepolyureaformaldehyde condensation reaction product, polyaminepolyureaepihalohydrine condensation reaction product, polyaminepolyureaformaldehyde condensation reaction product, polyamideaminepolyureaepihalohydrine condensation reaction product, and polyamideaminepolyureaformaldehyde condensation reaction product.

Many of these compounds were developed as waterproofing agents, printability improver, wet strength improver, paper strength reinforcing agent for papers. They were developed as chemicals to inhibit the formation of hydrogen bonds in paper. Reaction conditions and concentration of the compounds similar to those of the organic crosslinking agent provide comparable results.

The methods of producing the above-mentioned compounds are not limited to the general methods described hereinafter.

The polyamide compound (also called polyamideamine compound) is obtained by dehydration condensation reaction of a polyamine and a compound having carboxyl group.

The polyamidepolyurea, polyaminepolyurea, polyamideaminepolyurea and polyamideamine compounds are reaction products from polyalkylenepolyamine or alkylenepolyamine, urea, and dibasic carboxylic acid. The compounds can be modified with a small amount of aldehyde, epihalohydrine or $\alpha,\gamma$-dihalo-$\beta$-hydrine. The method of their production is described in Japanese Patent Publication (Kokoku) No.59-32597 and Japanese Patent Application Laid-Open (Kokai) No.4-10097.

The polyamideamine-epihalohydrine condensation reaction product, polyamideamine-formaldehyde condensation reaction product, polyamine-epihalohydrine condensation reaction product, polyamine-formaldehyde condensation reaction product, polyamidepolyurea- epihalohydrine condensation reaction product, polyamidepolyurea-formaldehyde condensation reaction product, polyaminepolyurea-epihalohydrine condensation reaction product, polyaminepolyurea-formaldehyde condensation reaction product, polyamideaminepolyurea-epihalohydrine condensation reaction product and polyamideaminepolyurea-formaldehyde condensation reaction product, are reaction products from polyalkylenepolyamine, urea, dibasic carboxylic acid, and epihalohydrine or formaldehyde. The manufacturing methods are described in Japanese Patent Publication (Kokoku) No.52-22982, Japanese Patent Publication (Kokoku) No.60-31948, Japanese Patent Publication (Kokoku) No.61-39435 and Japanese Patent Application Laid-Open (Kokai) No.55-127423.

A sizing agent for paper is a chemical, which makes the hydrophilic group of paper hydrophobic and prevents it from soaking up ink. This chemical also makes the carboxylated latex product non-adhesive. It is contemplated that the chemical makes the carboxyl group hydrophobic chemically, physico-chemically or physically. There is no established theory for the hydrophobicity-forming mechanism, but the sizing agent gives a large and stable effect since it has been developed as a sizing agent of paper.

Sizing agents for paper include internally added sizing agents and surface sizing agents. The invention can use any sizing agent on as long as it exhibits the ability to create a non-adhesive surface.

Internally added sizing agent can be classified as an acid sizing agent, a neutral sizing agent and an acid/neutral sizing agent (Japanese Patent Application Laid-Open (Kokai) No. 11-61682).

An acid sizing agent can include rosin sizing agent, fatty acid soap sizing agent, synthetic sizing agent and petroleum resin sizing agent.

Rosin sizing agents include rosins and rosin derivatives. The rosins refer to gum rosins, wood rosins and tall oil rosins which contain, as the main component, resin acids such as abietinic acid, palustric acid, neoabietinic acid, pimaric acid, isopimaric acid and dehydroabietinic acid.

Rosin derivatives include hydrogenated rosins, polymerized rosins, modified rosins, fortified rosins, rosin esters and fortified rosin esters.

Modified rosins include (alkyl)phenol-formalin resin modified rosins, xylene resin modified rosins, aldehyde modified rosins and styrene modified rosins.

Fortified rosins are obtained by heating and reacting the rosins and $\alpha,\beta$-unsaturated carboxylic acids.

Rosin esters are produced using rosins and polyhydric alcohols by known esterification.

Fortified rosins are obtained by successively or simultaneously reacting the rosins and/or the modified rosins with known polyhydric alcohols and $\alpha,\beta$-unsaturated carboxylic acids.

Fatty acid soap sizing agent is a sizing agent obtained by neutralizing a fatty acid having about 8 to 24 carbons such as palmitic acid or stearic acid and a mixture thereof with an alkali.

A synthetic sizing agent includes a sizing agent obtained by neutralizing with an alkali a substituted succinic anhydride obtained by reacting an oligomer, dimer or tetramer, of isobutene and a mixture thereof with maleic anhydride.

A petroleum resin sizing agent includes one obtained by modifying a petroleum resin with an unsaturated carboxylic acid such as maleic acid. The petroleum resin can be C5 petroleum resin obtained by polymerizing C5 olefin such as 1,3-pentadiene or isoprene, C9 type petroleum resin obtained by polymerizing C9 olefin such as coumarone or indene, C5/C9 copolymer type petroleum resin obtained by copolymerizing C5 olefin and C9 olefin, and dicyclopentadienc type petroleum resin obtained by polymerizing dicyclopentadiene or its derivative.

Neutral sizing agents include alkylketenedimer type, alkenylketenedimer type, alkenyl succinic anhydride type and neutral rosin type sizing agents.

Usually, an alkylketenedimer type or alkenylketenedimer type sizing agent can be produced by emulsifying an alkylketene dimer or alkenylketene dimer which is prepared by treating a saturated or unsaturated fatty acid chloride having about 12 to 24 carbons with a base such as triethylamine to make a dimer. The alkenyl succinic anhydride type sizing agent can be prepared by emulsifying an alkenyl succinic anhydride obtained by the addition of a terminal and/or internal olefin having about 12 to 24 carbons with maleic anhydride.

Neutral rosin sizing agents include polyhydric alcohol esters of rosins and emulsions made by dispersing petroleum resin-containing substances in water.

Polyhydric alcohol esters of the rosins include reaction products containing rosin esters obtained by reacting rosins with (a) at least one chemical belonging to the family of polyhydric alcohols and (b) at least one chemical belonging to the family of $\alpha,\beta$-unsaturated carboxylic acid or its derivative.

Acid/neutral sizing agents include cationized fatty acid bisamide type, cationized petroleum resin type, cationized polymer type and $\alpha$-hydroxycarboxylic acid type sizing agent.

Cationized fatty acid bisamide type and cationized petroleum resin type sizing agents are synthesized by reacting a maleic acid adduct of a fatty acid having about 12 to 24 carbons or a petroleum resin with a polyamine such as diethylenetriamine and triethylenetetramine and a mixture thereof, followed by a reaction with epichlorohydrine.

The cationic polymer type sizing agent is usually synthesized by radically polymerizing a cationic vinyl monomer, such as dimethylaminoethylmethacrylate, and a hydrophobic monomer, such as styrene, acrylonitrile or alkyl(meth) acrylate, in water and /or in an organic solvent.

The $\alpha$-hydroxycarboxylic acid type sizing agent is made by reacting a higher alcohol or higher amine with an oxyacid such as citric acid.

Surface sizing agents generally comprise a hydrophobic portion and an anionic portion such as a carboxyl group. The surface sizing agent is obtained by copolymerizing a hydrophobic monomer and an anionic monomer such as $\alpha,\beta$-unsaturated monocarboxylic acid, $\alpha,\beta$-unsaturated dicarboxylic acid and unsaturated sulfonic acid. (See Japanese Patent Application Laying-Open (kokai) No.12-45197.)

Examples of surface sizing agents which consist of a copolymer of a hydrophobic monomer and an anionic monomer include styrene-(meth)acrylic acid copolymer, styrene-(meth)acrylic acid-(meth)acrylic acid ester copolymer, styrene-maleic acid copolymer, styrene-maleic acid-maleic acid halfester copolymer, (di)isobutylene-maleic acid copolymer, (di)isobutylene-maleic acid-maleic acid halfester copolymer and salts of these.

Surface sizing agents, other than the above-mentioned, include alkylketene dimer, alkenyl succinic acid(anhydride), styrene-acrylic acid copolymer, acrylate-acrylonitrile copolymer, styrene-dialkylaminoalkyl(meth)acrylate copolymer, and these products reacted with epihalohydrine.

The carboxyl group blocking agent is not necessarily a crosslinking agent for the carboxyl group. If it is a substance which acts on the carboxyl group chemically, physicochemically, or physically, making the site hydrophobic and hindering the formation of a hydrogen bond, the agent makes the carboxylated latex product non-adhesive.

Consequently, even the compounds that cannot form crosslinking structures with the carboxyl groups, for example, monofunctional amines, monofunctional epoxy compounds, monofunctional isocyanates and monofunctional blocked isocyanates, can make the carboxylated emulsion latex product non-adhesive. Because they have only one functional group, crosslinking does not occur. However, if these compounds have hydrophobic groups, they react with carboxyl groups to result in hydrophobicity.

As for the amines, any primary, secondary, tertiary or quaternary amine can provide this effect.

A surfactant is composed of hydrophilic group and hydrophobic group. If the hydrophilic group is arranged towards the surface of the carboxylated emulation latex product and the hydrophobic group away from the surface, supposedly the carboxyl group of the product surface is blocked, resulting in hydrophobicity and making the surface non-adhesive. Accordingly, it is thought that the degree of hydrophobicity of the surfactant controls the degree of non-adhesion of the product. Whether the surfactant takes up the position on the product surface with the hydrophobic group directed to the outside is determined by the physical and chemical properties of the surfactant itself, the properties of the latex, addition or absence of aluminum compounds and the like. It is difficult to find a general rule. Therefore, it is necessary to select non-adhesion surfactants through the adhesion test 2 shown in the examples. The results of the test were that the surfactant showed a non-adhesion effect in situations where the internally added aluminum type inorganic crosslinking agent such as aluminum hydroxide gel and aluminate, was added to the emulsion latex. Presumably, the surfactant, viewed in light of its properties, diffuses throughout the latex film. The internally added aluminum type inorganic crosslinking agent is thought to suppress diffusion of the surfactant.

With respect to the nonionic surfactant, a general rule cannot be found. However, it can be said that a nonionic surfactant having a high HLB shows a low non-adhesion effect and that a nonionic surfactant of amine and amide types shows a high non-adhesion effect.

With cationic surfactants and amphoteric surfactants, the cations of the surfactant and the anions of the carboxyl group combine to form an ion linkage. Hence, many of these give good results when subjected to the above-mentioned adhesion test. However, since both surfactants react chemically with carboxyl groups at low temperatures, they influence the formation of the latex film in the dipping step if they are added to the coagulant. That is, depending on the type and concentration of the surfactant, fine wrinkles can be generated toward the direction of the dipping, and sometimes cracks can be generated. Further, if the surfactant diffuses internally into the film, it competes with the latex vulcanizing agent, such as zinc oxide, and hinders vulcanization to cause a decrease in the strength of the film. Consequently, countermeasures are needed for keeping the surfactant concentration low to suppress diffusion, accelerating vulcanization by raising the temperature of the drying and leaching process and so forth. However, these are big drawbacks to the manufacturing process. From the above-mentioned point, an adhesion test is needed to select the appropriate surfactant and its concentration.

It is unclear how an anionic surfactant provides the non-adhesive effect. Generally, an anionic surfactant is used as an emulsifier in synthesizing the carboxylated emulsion latex. Moreover, dodecybenzenesulfonic acid, for example, reacts with metal salts in the coagulant during dipping, converting most of it to metal soap, and losing its ability to function as a surfactant. Metal soaps, as seen from the fact that they are used as lubricating oil, have more or less adhesion. But, some anionic surfactants produce excellent non-adhesive effects. There are many effective surfactants among those that have amine and amide group in the structure and are considered to react with the carboxyl group and those that have a polycyclic structure and are considered to be highly hydrophobic. For example, the use of naphthalenesulfonic acid formaline condensation reaction products or alkylnaphthalenesulfonic acid formaline condensation reaction products is effective for producing a non-adhesive latex product. The above-mentioned rosin sizing agent falls into this category.

Surfactants, because of their properties, have a great effect on each manufacturing step of the carboxylated emulsion latex product and on the properties of the product. Therefore, in order to judge whether a surfactant is usable or not, it is necessary to confirm its ability to have a non-adhesive effect by conducting the adhesion test and, at the same time, studying the effect on the film formed and its quality.

There are a variety of methods for manufacturing the non-adhesive latex product of the invention.

When the product has already been formed into a film, it is possible to bring one surface or both surfaces of the product in contact with the carboxyl group blocking agent solution and to treat the carboxylated latex surface with the blocking agent. Depending on the kind of the carboxyl group blocking agent, the reaction can be very fast, and by the time the product is taken out of the solution, the latex film surface may have already lost its adhesiveness. In other situations, heating is needed after the product has been taken out of the solution. Either way, to obtain the full effect of the treatment, it is desirable to conduct a heating step.

In the case of a dipped product, by depositing one or more carboxyl group blocking agents and an usual external coagulant onto the dipping former and then bringing it into contact with the emulsion latex, coagulation of the latex and treatment with the blocking agent can be conducted at the same time.

There are four methods for depositing the carboxyl-group blocking agent on the dipping former. The first method is one wherein an external coagulant consisting of mono- or bi-valent metal salts and one or more of the carboxyl group blocking agent of the invention are mixed, dissolved, and deposited onto the dipping former. The second method is one wherein the carboxyl-group blocking agent of the invention is deposited onto the dipping former and, thereafter, an external coagulant is deposited onto the formed layer. Modifying this method gives a method wherein the carboxyl group blocking agent is incorporated into the emulsion carboxylated latex, the dipping former is dipped in said formulation liquid to form a thin latex film, the former is dipped in a mono- or bivalent external coagulation solution, and then the former is dipped in the carboxylated latex solution again.

The third method is one wherein one or more of the powdery carboxyl blocking agents of the invention is used as a support. The carboxyl group blocking agent is suspended in an external coagulant solution and then deposited onto the dipping former. This method does not give a perfect non-powder product, but, since the carboxyl-group blocking agent reacts with the latex and is absorbed, the powder can be reduced to such a degree as to be unable to be perceived on the finished product.

By immersing such dipping former in the emulsion latex, there is obtained a dipped product in which the inside surface contacting the former is non-adhesive.

The fourth method is one wherein a thin, carboxyl group blocking agent treated film of the latex is formed by using the carboxyl group blocking agent as an external coagulant, the external coagulant consisting of a mono- or bi-valent metal compound is deposited onto the film, and the former is dipped in the latex liquid again. With this method it is possible to make the inside surface non-adhesive, but it is feared that peeling may occur between the layers of the product.

Further, the outside surfaces can be made non-adhesive by the above-mentioned methods.

In the case of cast-mold products, the inside surface of the mold is treated only with the carboxyl group blocking agent of the invention.

As mentioned above, it is possible, by using the present invention to fabricate a latex product non-adhesive in one or both surfaces. The surfaces of such products do not adhere together when each surface comes into contact with the other under heating during and after the manufacturing process.

Accordingly, by utilizing this property, a product can be produced that has never existed until now.

One such product is a non-adhesive fingerstall mechanically wound (rolled) from its mouth before being removed from the dipping former. Fingerstalls wound from the mouth are known and their usefulness have been recognized because of their ease in use. However, both surfaces of a fingerstall, a latex product, are intrinsically adhesive. In order to manufacture the wound product, the fingerstall had previously been made non-adhesive by treatments such as powdering and post-chlorination, followed by winding with human hands. This makes it impossible to maintain the high degree of cleanliness of the product needed for its use in workplaces where precisely processed articles are manufactured, such as in clean rooms. The present invention, however, which is able to make both surfaces of the latex molding non-adhesive, allows for mechanical winding of the fingerstall on the dipping former and can therefore, maintain a high degree of cleanliness of the product.

Recently, thin fingerstalls are desired since wearing thick ones tend to cause exhaustion. The thinner the fingerstall, however, the more difficult it is to use. Accordingly, what is desired is a wound fingerstall that is easy to use, thin, powder-free, non-adhesive and clean.

By utilizing the property that both surfaces of the fingerstall are non-adhesive, fingerstalls wound at the mouth can easily be manufactured. In manufacturing the fingerstall, the top of the stall is left adhesive without providing the layer of the carboxyl group blocking agent, the whole can be wound up, and then unwound. The portion having adhesion remains as a rolled lip. Hitherto, the rolled lip had been formed first by winding up only the top of the stall to make the rolled lip, and, thereafter, the stall had to be released from the former in another step. The rolled lip facilitates donning and doffing of the stall and is highly desirable for flat products. Further, after formation of the rolled lip according to the prior art, non-adhesion treatment can be conducted to achieve the objective.

The present invention is explained in detail using examples hereinafter, but the invention is not limited to the examples. The percentages and amounts per part shown in the examples are percentages by weight and parts unless otherwise indicated. Further, in the examples mentioned below, unless otherwise indicated, the latex film was prepared by the dipping method because of the ease of conducting the experiments and ease in confirming the effect. The present invention, however, is not limited to dipping products and methods of manufacturing dipped products.

(Preparation of Latex Film)

Using a test tube shaped, glass dipping former for making fingerstalls, a latex film was prepared. When an external coagulant and a carboxyl-group blocking agent of solution types were used, a sand-blasted glass dipping former was used. When a powdery carboxyl-blocking agent was used, a transparent glass dipping former not subjected to sand blasting was used. First, the dipping former was dipped in the external coagulation liquid, to coat the former, and dried. Next, the dipping former was dipped in a latex emulsion to form a latex film, dried, leached and subjected to a vulcanization treatment according to conventional methods.

In cases where the outside surface of the film is to be treated, the dipping former affixed with the film is dipped in a solution or suspension liquid of a carboxyl group blocking agent, followed by drying and leaching steps.

The latex used is a carboxylated NBR, NIPOL LX-551, made by Nippon Zeon, unless otherwise specified. The latex, however, is not limited to this type. The properties of LX551 are shown below.

Solids 45%

PH 8.5

Viscosity 85 mPs

Gel content 0%

Tg −14

Combined AN content 37%

To 100 parts of the above-mentioned latex, fine zinc oxide was added as a vulcanizing agent, and the mixture was subjected to the following test.

(Adhesion Test of Latex Film-1)

The adhesion of the latex film is highest when the film is heated in a water-containing state.

After the leaching step, following the non-adhesion treatment of the outside surface in the film manufacturing process, the latex film is wound on the dipping former and removed from the dipping former. This sample is heated in a hot air dryer at 70° C. for 30 minutes, taken out and unwound after cooling. The film is thick because it is wound, and the sample is always in a wet condition during the test. Accordingly, if both surfaces of the film are non-adhesive, unwinding is easy. If adhesive, unwinding is difficult.

COMPARATIVE EXAMPLE 1

(Preparation of External Coagulation Solution)

A solution of calcium nitrate tetrahydrate 150 g and water or methanol 1000 g was prepared to make an external coagulant (hereinafter called coagulant 1).

(Manufacture of Latex Film)

A sand-blasted glass pipe is dipped in the aqueous external coagulant 1 and dried. The glass pipe coated with the external coagulant is dipped in a latex emulsion to form a latex film. The film affixed on the dipping former is dried softly at 50° C. for 3 minutes and further subjected to the leaching treatment for 3 minutes in hot water at 70° C. Subsequently, the film is wound on the former and released from the former. The film is unwound and subjected to a vulcanization treatment in a hot air dryer at 120° C. for 30 minutes to make samples to test their strength. For the adhesion test, the sample wound and removed from the former was presented as it stood. The sample after the adhesion test could not be unwound. The test results of film strength and adhesion are shown in Table 1.

EXAMPLE 1

The film formed in Comparative Example 1 is leached, released from the former, unwound, dipped in an aqueous solution of polyaluminumchloride (which is an external crosslinking agent) containing 2.5% alumina and immediately taken out. At this time, the film surface already has lost its adhesiveness and has a feeling of smoothness. This film, dried at 70° C. for 3 minutes, is further subjected to a leaching treatment in hot water at 70° C. for 3 minutes, and subjected to a vulcanization treatment in the same manner as Comparative Example 1. The results of the strength test of the film are shown in Table 1. For the adhesion test, the film, which underwent leaching treatment after non-adhesion treatment of the outside surface, was again placed on the former. The film was wound to make test samples. The sample after the adhesion test could easily be unwound.

EXAMPLE 2

The dipping former was dipped in a solution of polyaluminum chloride (which is an external coagulant) containing 2.5% alumina and used in Example 1 to coat the former, then dried, next dipped in the external coagulant methanol solution 1 and dried. Then the dipping former was dipped in the latex liquid to form a film, then dried at 50° C. for 3 minutes and further subjected to a leaching treatment at 50° C. for 3 minutes. Thereafter, the former was again dipped in the aqueous solution of polyaluminum chloride used in Example 1 in order to prevent the adhesion of the film's outside surface and subjected to a leaching treatment and a vulcanization treatment. The test results on the film strength are shown in Table 1. The sample, after the adhesion test, was able to be unwound easily. This shows that the inside surface of the film contacting the dipping former had become non-adhesive. The outside surface is also non-adhesive, as in Example 1.

EXAMPLE 3

In this example, aluminum acetate, containing 2.4% alumina was used in place of polyalunimun chloride, was coated on the dipping former by dipping. The latex film was prepared as in Example 2 and was dipped with the former. Table 1 shows the test results on the strength of the film. The film wound in the adhesion test could easily be unwound.

EXAMPLE 4

Using aluminum nitrate containing 0.2% alumina and a solution containing calcium nitrate tetrahydrate 150 g and methanol 1000 g as an external coagulation liquid and external crosslinking liquid, a film was produced. Adhesion preventing treatment of the outside surface of the film according to the same procedure as in Example 2 was performed. The film thickness was approximately equal to that of Comparative Example 1 and Example 2. The test results on the strength of the film are shown in Table 1. In this case too, as with Example 2, the sample after the adhesion test could easily be unwound.

COMPARATIVE EXAMPLE 2

The dipping former was dipped in the external crosslinking agent, polyaluminum chloride solution, used in Example 1, and a film was formed in the same manner as Comparative Example 1. The film thickness was only 0.03 mm and the polyaluminum chloride was found to be unsuitable as an external coagulant. Using various aluminum compounds such as aluminum chloride, aluminum nitrate and aluminum acetate, the same tests as above were conducted. The results were the same.

COMPARATIVE EXAMPLE 3

The order of attaching the external crosslinking agent and the external coagulant to the former in Example 2 was reversed, and the dipping treatment was conducted so that the layer of polyaluminum chloride is found on the outside surface. The thickness of the film was only 0.04 mm, being similar to Comparative Example 2. This method was unsuitable for external coagulant formulation.

REFERENCE EXAMPLE 1

A latex film was prepared in the same way as Example 3 except that fine zinc oxide was not added in the emulsion latex. As with Example 3, the film formed had the usual thickness, and both surfaces of the film were non-adhesive. On the other hand, the strength of the film was extremely low. It may be that the aluminum crosslinking layers are extremely thin and they do not contribute to film strength.

COMPARATIVE EXAMPLE 4

A latex film was prepared in the same way as Example 1 except that an aqueous solution of zinc nitrate containing 5% zinc oxide was used in place of polyaluminum chloride. The film was adhesive, and it was impossible to unwind the wound fingerstall after the adhesion test. Zinc is bivalent and insufficient to make the film non-adhesive.

Table 1 shows the test results on film strength.

EXAMPLE 5

An aqueous solution of sodium aluminate and an aqueous solution of calcium nitrate were mixed to prepare calcium aluminate. A solution of water/methanol(1/1) was prepared to make calcium aluminate 20 g/1000 g (calculated as anhydride) and calcium nitrate tetrahydrate 150 g/1000 g.

A transparent glass dipping former was dipped in the external coagulation liquid. A coagulant layer was formed on the former using calcium aluminate as a support. A latex film was prepared in the same way as Example 2.

On the dipping former calcium aluminate coated thinly, but when the inside surface, after vulcanization, was observed, the calcium aluminate was barely noticeable. The sample, after the adhesion test, could be unwound. The test results of the film strength are shown in Table 1.

When the dipping former is vigorously shaken immediately after the latex film is formed by dipping in the emulsion latex, the latex film breaks down. Under the latex layer, a very thin aluminum treatment layer is present. Taking into consideration this fact and Reference Example 1, it is evident that the aluminum treatment layer is a very thin layer.

EXAMPLE 6

Dry aluminum hydroxide gel made by Tomita Seiyaku Co. was dispersed with a ball mill for 24 hours and then added to water and methanol so that a suspension of aluminum hydroxide 20 g (calculated as anhydride) in 1000 g water/methanol(1/1) and calcium nitrate tetrahydrate 150 g in 1000 g water/methanol(1/1) was prepared. Thereafter, a latex film was formed in the same manner as Example 5. The test results on strength are shown in Table 1. The wound film could easily be unwound as with

EXAMPLE 4.

In the process of heating the film, it was observed that aluminum hydroxide is absorbed into the latex film.

COMPARATIVE EXAMPLE 5

There was prepared a suspension solution of water/methanol(1/1) having light calcium carbonate 100 g 1000 g, bentonite 50 g/1000 g and calcium nitrate tetrahydrate 150 g/1000 g. A latex film was manufactured in the same manner as Example 5.

The wound latex film could not be unwound even before heating. A sample for testing the strength was prepared using talc as the powder to provide the non-adhesive effect.

COMPARATIVE EXAMPLE 6

A latex film was made in the same manner as Comparative Example 1 except that 1 part of aluminum hydroxide used in Example 6 (calculated as anhydride) was added to 100 parts of a latex. The wound film could not be unwound.

EXAMPLE 7

Using an aqueous solution containing 0.2% aluminum nitrate (as alumina) and 150 g calcium nitrate tetrahydrate in 1000 g water as the external coagulant and concurrently as the external crosslinking agent, a latex film was fabricated. Thereafter, the outside surface of the film was dipped in an aqueous solution of zirconyl acetate, 1.5% $ZrO_2$, and leaching and vulcanizing treatments were conducted in the same manner as Example 2. The results of the strength test on the film are shown in Table 1. The sample, after the adhesion test, could easily be unwound.

EXAMPLE 8

Using an aqueous solution containing 0.2% zirconyl nitrate ($ZrO_2$) and 150 g calcium nitrate tetrahydrate in 1000 g water as the external coagulant and concurrently as the external crosslinking agent, a latex film was prepared. Thereafter, the outside surface of the latex film was dipped in an aqueous solution of polyaluminum chloride (2.5% alumina), leaching and vulcanizing treatments were conducted in the same manner as Example 2. The results of the strength test for the film are shown in Table 1. The sample, after the adhesion test, could easily be unwound.

EXAMPLE 9

A latex film was prepared in the same manner as Example 7, except that an aqueous solution of titanium lactate of 1.5% $TiO_2$ was used in place of zirconyl acetate. The results of the strength test for the film are shown in Table 1. The sample, after the adhesion test, could easily be unwound.

EXAMPLE 10

An adhesion test of a latex film was conducted in the same manner as Example 4, except that carboxylated SBR (SBR 2570X5 made by Nippon Zeon Co.) was used in place of NBR. The sample, after the adhesion test, could easily be unwound. Zinc oxide was not incorporated into SBR in the experiment.

EXAMPLE 11

A latex film was prepared in the same manner as in Example 5 except that carboxylated CR latex mentioned below was used in place of NBR. The results of the strength test for the film are shown in Table 1. The sample, after the adhesion test, could easily be unwound.

Carboxylated CR latex made by Toso Co.
GFL-280 60 parts
LA-502 40 parts
(further containing Zinc oxide made by Seido Kagakusha Co., 5 parts)

The pH and viscosity of the formulation latex was 8.9 and 37.8 mPs, respectively.

COMPARATIVE EXAMPLE 7

A latex film was formed using the carboxylated CR latex used in Example 10 and using calcium nitrate as an external coagulant. The film, thus formed, had strong adhesiveness and was impossible to remove from the dipping former. This latex can be used as an adhesive.

TABLE 1

| | Thickness of film (mm) | Maximum load stress (kgf/cm$^2$) | Maximum load strain (%) | Adhesion test | Remarks |
|---|---|---|---|---|---|
| Example 1 | 0.11 | 390 | 680 | Possible to unwind | |
| Example 2 | 0.12 | 370 | 695 | Possible to unwind | |
| Example 3 | 0.12 | 370 | 680 | Possible to unwind | |
| Example 4 | 0.12 | 380 | 690 | Possible to unwind | |
| Example 5 | 0.13 | 480 | 790 | Possible to unwind | |
| Example 6 | 0.09 | 450 | 720 | Possible to unwind | |
| Example 7 | 0.11 | 290 | 700 | Possible to unwind | |
| Example 8 | 0.10 | 300 | 720 | Possible to unwind | |
| Example 9 | 0.11 | 310 | 680 | Possible to unwind | |
| Example 11 | 0.12 | 256 | 1040 | Possible to unwind | |
| Example 12 | 0.12 | 340 | 732 | Possible to unwind | Easy to wear |
| Example 13 | 0.11 | 350 | 650 | Possible to unwind | Very easy to wear |
| Reference Example 1 | 0.09 | 30 | 640 | Possible to unwind | Poor strength |
| Comparative Example 1 | 0.12 | 410 | 690 | Impossible to unwind | |

TABLE 1-continued

|  | Thickness of film (mm) | Maximum load stress (kgf/cm$^2$) | Maximum load strain (%) | Adhesion test | Remarks |
|---|---|---|---|---|---|
| Comparative Example 2 | 0.03 | Not determined | Not determined | Not tested | Defect of film thickness |
| Comparative Example 3 | 0.04 | Not determined | Not determined | Not tested | Defect of film thickness |
| Comparative Example 5 | 0.08 | 530 | 750 | Impossible to unwind | |
| Comparative Example 6 | 0.07 | 490 | 760 | Impossible to unwind | |

EXAMPLE 12

Figure 2:
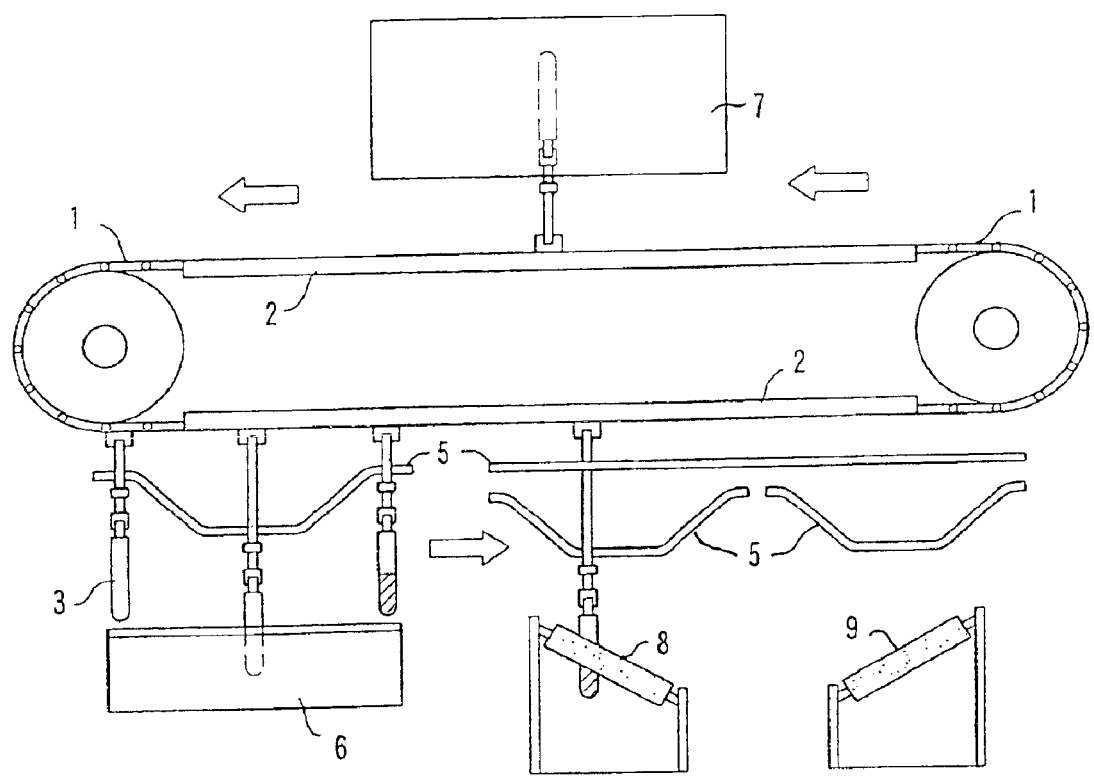
FIG. 2 shows the trial apparatus for manufacturing the fingerstall used in the examples. There is shown a dipping tank 6, a drying furnace 7, a winding machine 8, and an unwinding machine 9.

An instrument for manufacturing fingerstalls, as shown in FIG. 2, is equipped with a dipping former transferring apparatus (see Japanese Patent Application Laying-Open (kokai) No.7-329084). Using this instrument, fingerstalls were produced in the same manner as Example 2 to Example 6. The dipping former transferring apparatus of FIG. 1 transfers the dipping former 3 with its chain 1, which moves along the guide rail 2.

Figure 3:
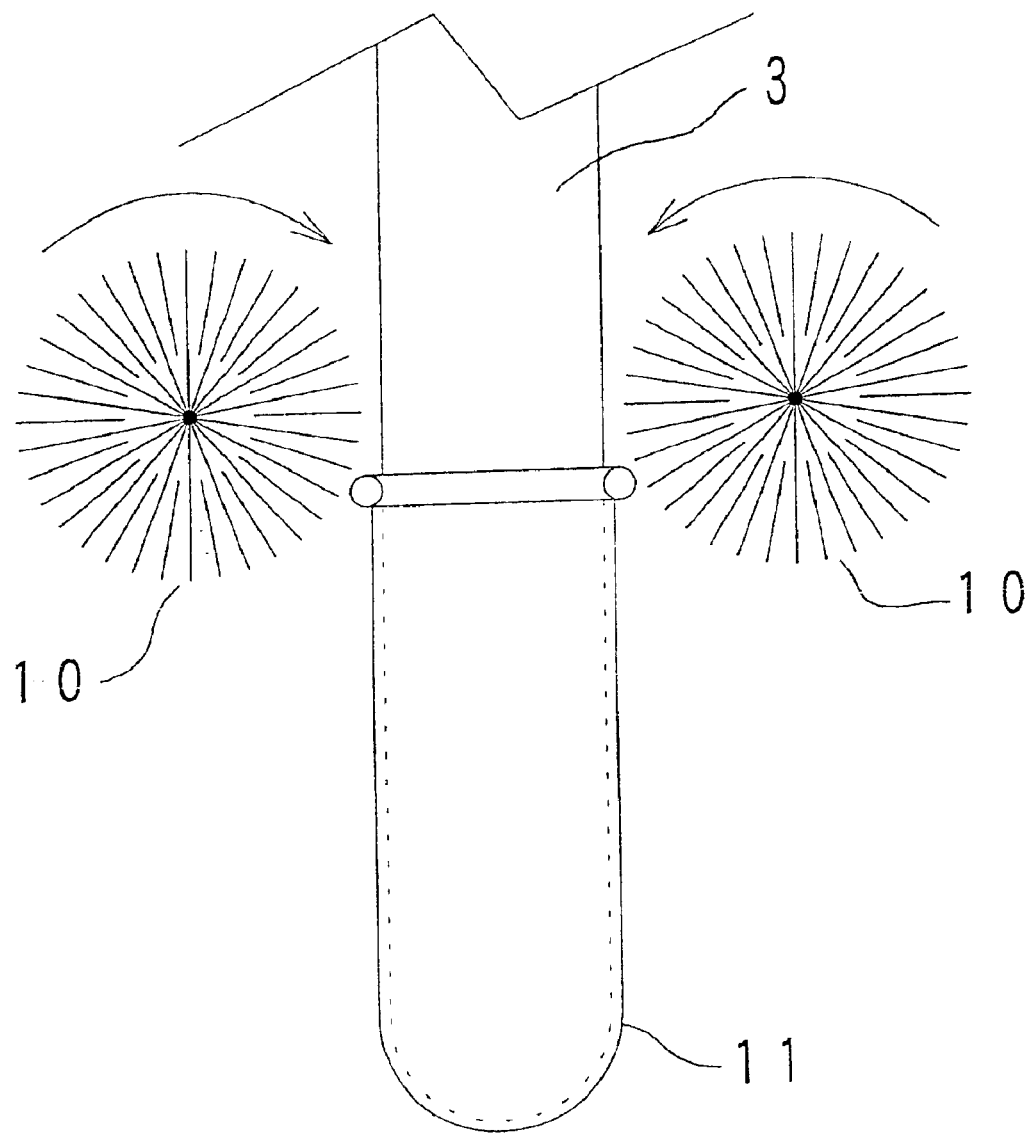
FIG. 3 shows the main parts of the winding machine. There is shown a rolling brush 10 and a film 11.

A rod 4 moves along the guide 5 and enables the dipping former 3 to move upwards and downwards. In FIG. 2, when the dipping former 3 reaches a dipping tank 6, the dipping former 3 is lowered into the dipping tank. The external crosslinking solution tank, external coagulation solution tank, latex liquid tank and leaching treatment tank have previously been made ready. The tanks are switched when deemed necessary, and each applicable dipping treatment and leaching treatment is carried out in series. After each dipping treatment and leaching treatment, the dipping former 3 is transferred to a drying furnace 7 and dried. Except when a winding machine 8 and an unwinding machine 9 are used, the dipping former 3 is kept so that it is not brought downwards so that it does not come into contact with the winding machine 8 and the unwinding machine 9. During the drying and leaching treatment, the dipping former 3 is stopped for a sufficient period to undergo the treatments. The winding machine 8 rotates a roll type brush 10 (FIG. 3) previously set up obliquely. By passing the dipping former through the brush 10, the film 11 coating the dipping former 3 is wound. Thus, after the leaching and subsequent drying treatments, the dipping former 3 is passed through the winding machine 8 and the film deposited on the dipping former is wound before being removed from the former.

A wound fingerstall made by the above instrument is dried at 70° C. for 120 minutes to finish the product. This stall was easy to don on the finger. The wound film was immediately unwound, dried at 70° C. for 60 minutes and subjected to the film strength test.

EXAMPLE 13

Figure 4:
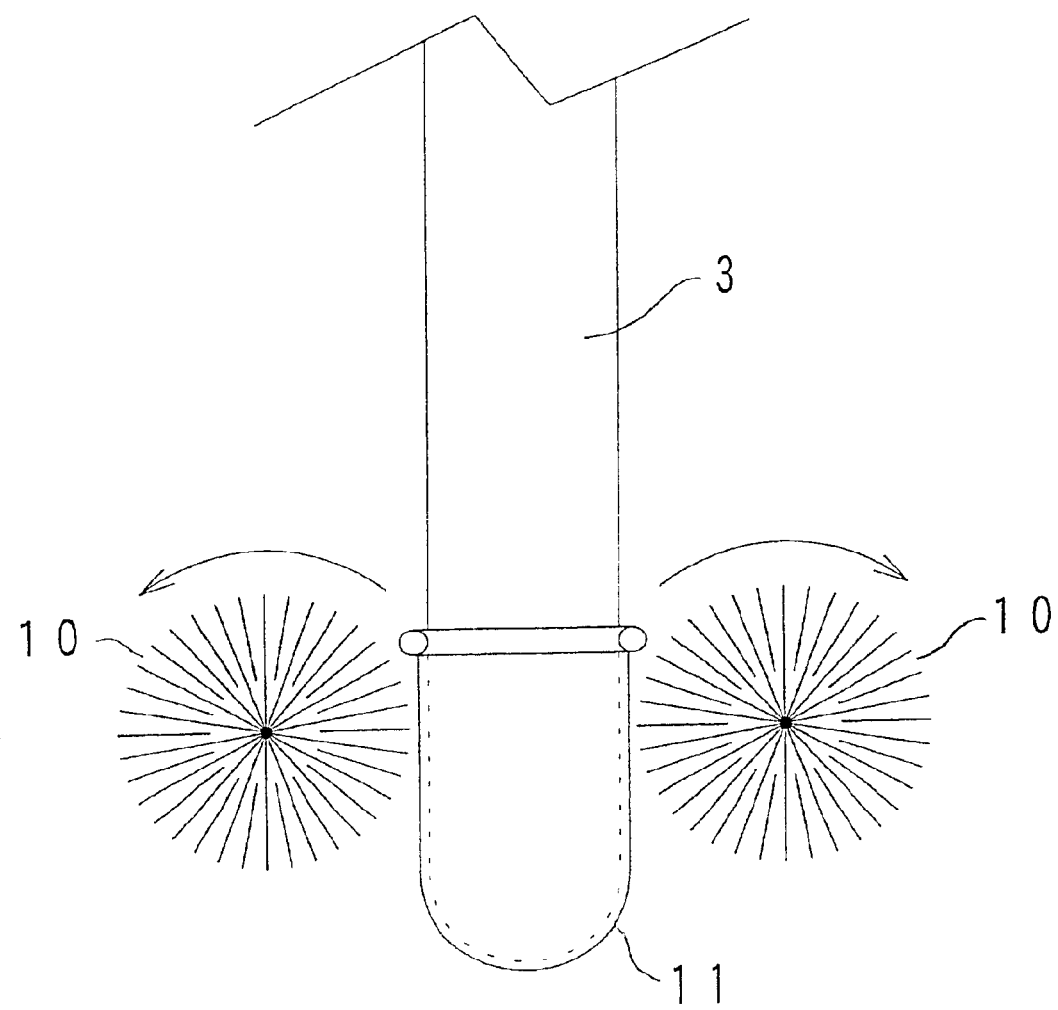
FIG. 4 shows the main parts of the unwinding machine.

In the same manner as described in Example 12, the dipping former was passed through the winding machine and the wound fingerstall was unwound by the unwinding machine 9. The unwinding machine 9, as shown in FIG. 4, rotates a roll type brush 10, and when the dipping former 3 is passed there, the machine unwinds the film 11 wound by the winding machine 8. The unwound fingerstall was dried in the drying furnace 7 at 90° C. for 5 minutes. After drying, the stall was again treated on the winding machine 8 and removed from the former to obtain the wound fingerstall.

This method of manufacturing the stall is evaluated to be highly practical, because drying the product is easy and the stall is easy to put on and take off the finger because the winding operation is conducted twice. The films were dried at 90° C. for 5 minutes prior to film strength testing.

EXAMPLE 14

In the same manner as described in Examples 12 and 13, wound fingerstalls were prepared by the winding machine 8, but the manufacturing conditions were changed as follows. Namely, the dipping former was dipped in the latex liquid 1 cm more deeply than the portion deposited with the coagulant. Further, it was dipped in the external crosslinking agent 2 mm more shallowly than the portion where the coagulant is deposited. When these stalls are unwound, the adhesive portions remain as a rolled lip. The unwound fingerstalls are straight fingerstalls with a rolled lip and the fingerstalls before unwinding are wound fingerstalls with rolled lip.

EXAMPLE 15

(Wear Durability Test)

A fingerstall of a non-adhesive carboxylated latex vulcanized with zinc oxide showed very good strength in the strength test. But it was found that, when it was worn, the portion of the fingerstall that was in contact with finger joints and finger bottoms broke in some cases within several hours. It may be that expansion and contraction, which occurs during normal wear, may cause the ionic crosslink points to gradually break down. This phenomenon would most likely not occur in the case of sulfur vulcanization because they produce covalent bonds.

Ten slender fingerstalls (16.5 mm in diameter) were worn on the middle finger or the ring finger to investigate the number of stalls which will break after 24 hours. The results are shown in Table 2. When the emulsion latex is directly added with zinc oxide and an internally added aluminum type inorganic crosslinking agent such as aluminate and aluminum hydroxide gel (0.10 to 0.30 part Al$_2$O$_3$), and the latex film undergoes vulcanization, surprisingly the fingerstalls did not break. Presumably, when the crosslink points of zinc break, the aluminum ions crosslink and replace the broken crosslink points. The results are shown in Table 2 (also, refer to Table 12.)

The latex film forming conditions were the same as described in the paragraph mentioned below. Polyaluminum hydroxide chloride (Paho#2S, an aqueous solution of 0.025% Al$_2$O$_3$) was used as a carboxyl group blocking agent. The vulcanization temperature was 90° C.

The compounds used in the examples are as follows:

Aluminumhydroxide gel Aluminum hydroxide gel [Tomita] (made by Tomita Seiyaku Co.)

Sodium aluminate Sodium aluminate #2019 (made by Asada Kagaku Co.)

Polyaluminum hydroxide chloride Paho#2S (made by Asada Kagaku Co.)

TABLE 2

| | Example No. 15 | | | | | |
|---|---|---|---|---|---|---|
| Content of added NaAlO$_2$ (as Al$_2$O$_3$) (part) | 0 | 0.10 | 0.15 | 0.20 | 0.25 | 0.30 |
| Number of broken stalls after 24 hour-wearing | 10 | 5 | 2 | 0 | 0 | 0 |
| Content of added aluminumhydroxide gel (as Al$_2$O$_3$) (part) | 0 | 0.10 | 0.15 | 0.20 | 0.25 | 0.30 |
| Number of broken stalls after 24 hour-wearing | | | 2 | | 0 | |

(Screening of Carboxyl Group Blocking Agent)

This screening was conducted for carboxyl-group blocking agents other than the external crosslinking agents of metal compounds having three or more valences. These compounds generally have low reactivity with carboxyl groups at low temperatures. Because of this, these compounds tend to diffuse in the Z-axis direction of the latex film during the steps of dipping and leaching. To reduce the defect of the diffusion of the carboxyl-group blocking agent and to hinder the decrease in film strength, the latex was diluted to half the original concentration and the concentration of calcium nitrate, an external coagulant, was increased to 300 g/1000 g from 150 g/1000 g. Further, as mentioned below, with respect to the reaction temperature of the latex film before its strength is tested, because a higher temperature is desirable for good strength, the temperature at the leaching step was changed to 75° C. Further, to study the effect of the temperature at the vulcanization step, the vulcanization temperature was set at two levels, 90 and 120° C. The latex film forming conditions and the adhesion test conditions are as follows, unless otherwise specified.

(Latex Film Forming Conditions)
  Raw material latex: carboxylated NBR Nipol LX-551
  Vulcanizing agent: active zinc oxide 1.5 parts
    Sodium aluminate or aluminum hydroxide 0.25 part (as Al$_2$O$_3$)
  Solids concentration: adjusted to 22.5% by diluting with water(dilution, 1:2)
  Coagulant: calcium nitrate tetrahyrate; 300 g/1000 g
    Carboxyl group blocking agent: 0.025% or 0.0025%
    The dipping former is dipped in the coagulant solution. The amount deposited onto the former is adjusted to 0.03 g.
  Dipping: The dipping former attached with the coagulant is dipped in the latex solution. The dipping former is pulled up after 5 seconds
  Primary drying: 50° C., 2 minutes
  Leaching: 75° C., 3 minutes
  Drying: 90° C., 1 minute
  Outside surface treatment with carboxyl group blocking agent:
    The latex film is dipped in the outside surface treatment solution of 0.025% or 0.0025% carboxyl group blocking agent. The amount attached to the surface was 0.03 g.
  Vulcanization: The latex film was vulcanized at 90 or 120° C. for 5 minutes. The thickness of the latex film after vulcanization was 0.07 to 0.08 mm and the weight was 0.3 g.

(Adhesion Test-2)

The latex film prepared under the above-mentioned conditions is vulcanized, wound on the dipping former, and removed from the former as it is. The sample is heated in a hot air dryer for 90° C. for 30 minutes. Then, the sample is taken out from the dryer, cooled and unwound. The mark ○ indicates that unwinding is easy, the mark Δ indicates that unwinding becomes difficult on the way, the mark x indicates that unwinding is considerably difficult and the mark ○' indicates that unwinding is slightly problematic.

EXAMPLES 16 TO 18

To confirm the effect of the addition of the aluminum type inorganic crosslinking agent with is internally added in the emulsion latex (aluminum hydroxide gel in Examples 16 to 18, sodium aluminate in Examples 35 and 61), and the aluminum type external crosslinking agent for surface treatment (aluminum nitrate and polyaluminum_hydroxide chloride in Example 16, oxazoline compound in Example 17, and carbodiimide compound in Example 18), studies of the effect of the concentration of the carboxyl group blocking agent were conducted. Here, the vulcanization temperature of the aluminum type external crosslinking agent (aluminum nitrate or polyaluminum hydroxide chloride) was 90° C., and that of oxazoline and carbodiimide compounds was 120° C.

In the case of the aluminum type external crosslinking agent, even when the emulsion latex does not contain the internally added aluminum type inorganic crosslinking agent, the latex product becomes non-adhesive. When the internally added aluminum type inorganic crosslinking agent is used, the concentration of the carboxyl group blocking agent needed to treat the surface is less.

On the other hand, in the case where the carboxyl group blocking agent to treat the surface is a water-soluble oxazoline compound or water-soluble carbodiimide compound, if the internally added aluminum type inorganic crosslinking agent is not added, the effect of the carboxyl-group blocking agent on non-adhesiveness is small. However, although classified as compounds of the same kind, when the carboxyl group blocking agent is an emulsion type carboxyl group blocking agent, even when the internally added aluminum type inorganic crosslinking agent is not added, the non-adhesive effect on the surface is obtained. In the case of a water-soluble carboxyl group blocking agent to treat the surface, the carboxyl-group blocking agent diffuses in the Z-axis direction to result in the small effect by the carboxyl-group blocking agent. On the other hand, if the internally added aluminum type inorganic crosslinking agent is added, the diffusion of the carboxyl-group blocking agent is hindered, and, thus, a non-adhesive effect appears. The results are shown in Table 3. The compounds used in this example are as follows.

Aluminum hydroxide gel: aluminum hydroxide gel [Tomita] (made by Tomita Seiyaku Co.)

Polyaluminum hydroxide chloride: Paho#2S (made by Asada Kagaku Kogyo Co.)

Oxazoline compound: Epocross W (aqueous solution) (made by Nihon Shokubai Co.)

Epocross K-2030(emulsion) (made by Nihon Shokubai Co.)

Carbodiimide compound: Carbodilite E-01(emulsion) (made by Nisshinbo Co.)

Carbodilite V-02(aqueous solution) (made by Nisshinbo Co.)

Example 35 used a modified polyamine polyurea resin (Sumirez Resin 712). This resin is so reactive that it causes the latex to coagulate when added to the latex. With these compounds, much like the aluminum type external crosslinking agent, non-adhesive effects appear even if an internally added aluminum type inorganic crosslinking agent is not added. Further, alkylketene dimer of Example 61, an emulsion, is reactive, as is the emulsions of Examples 17 and 18, so even if an internally added aluminum type inorganic crosslinking agent is not added, they have a non-adhesive effect.

EXAMPLE 19

To study the influence of the diffusion of the carboxyl group blocking agent for treating a surface, the effect of temperature at the leaching step before vulcanization was studied.

The water-soluble oxazoline compound (Epocross W, made by Nippon shokubai Co.) was used as the carboxyl-group blocking agent. The concentration was varied from 0.1% to 0.001%, and the temperature at the leaching step was varied from 50 to 75° C. The results are shown in Table 4.

For concentrations as high as 0.1%, when the leaching step temperature is low, the film strength becomes low and the non-adhesive effect tends to be low.

Even when an internally added aluminum type inorganic crosslinking agent (sodium aluminate, 0.25 part $Al_2O_3$) was added, the influence of the diffusion at low temperatures could be noted.

TABLE 3

Content of internally added aluminum type inorganic crosslinking agent (as $Al_2O_3$) (part)

| Example No. | Carboxyl-group blocking agent for surface treatment | Trademark | | Vulcanization temp. | Concentration of Chemical | | | | |
|---|---|---|---|---|---|---|---|---|---|
| | | | | | 1.0% | 0.25% | 0.025% | 0.0025% | 0.001% |
| | | | Aluminum hydroxide gel | | | | | | |
| 16 | Aluminum compound | Al(NO₃)₃ (aq. solution) | 0 | 90° C. | ○ | ○ | ○' | x | |
| | | | 0.25 | 90° C. | | ○ | ○ | Δ | |
| | | Paho#2S (polyaluminum hydroxide chloride) (aq. solution) | 0 | 90° C. | | ○ | ○ | x | |
| | | | 0.25 | 90° C. | | ○ | ○ | Δ | |
| 17 | Oxazoline compound | Epocross K2030 (emulsion) | 0 | 120° C. | ○ | Δ | | | |
| | | | 0.25 | 120° C. | | ○ | ○ | ○ | |
| | | Epocross W (aq. solution) | 0 | 120° C. | x | x | | | |
| | | | 0.25 | 120° C. | | ○ | ○ | ○ | ○ |
| 18 | Carbodiimide compound | Carbodilite E-01 (emulsion) | 0 | 120° C. | ○ | ○ | Δ | | |
| | | | 0.25 | 120° C. | | ○ | ○' | Δ | |
| | | Carbodilite V-02 (aq. solution) | 0 | 120° C. | Δ | x | | | |
| | | | 0.25 | 120° C. | | ○ | ○ | Δ | |
| | | | Sodium aluminate | | | | | | |
| 35 | Modified Polyamine polyurea resin | Sumirez Resin 712 (aq. solution) | 0 | 90° C. | ○ | ○ | ○ | x | |
| | | | 0 | 120° C. | ○ | ○ | ○ | x | |
| | | | 0.25 | 90° C. | ○ | ○ | ○ | ○' | |
| | | | 0.25 | 120° C. | ○ | ○ | ○ | ○' | |
| 61 | Alkylketene dimer | Hasize AK-720H (emulsion) | 0 | 90° C. | ○ | ○ | ○ | | |
| | | | 0 | 120° C. | ○ | ○ | ○ | | |
| | | | 0.25 | 90° C. | | | ○ | ○ | |
| | | | 0.25 | 120° C. | | | ○ | ○ | |

TABLE 4

| Example No. | Carboxyl-group crosslinking organic agent for surface treatment | Conc. | | Temp. of leaching step | | | | | |
|---|---|---|---|---|---|---|---|---|---|
| | | | | 50° C. | 55° C. | 60° C. | 65° C. | 70° C. | 75° C. |
| 19 | Oxazoline compound Epocross W | 0.1% | Adhesion test | x | ○ | ○ | ○ | | ○ |
| | | | Strength (Mpa) | | 27.9 | 31.8 | 29.8 | 30.5 | 37.7 |
| | | 0.025% | Adhesion test | x | ○ | ○ | ○ | ○ | ○ |
| | | | Strength (Mpa) | | | | | | 37.3 |
| | | 0.005% | Adhesion test | | | | | | |
| | | | Strength (Mpa) | | | | | | 35.1 |
| | | 0.001% | Adhesion test | x | | | | | ○ |
| | | | Strength (Mpa) | | | | | | 35.1 |

EXAMPLE 20 TO 27

Studies of how the concentration of the compounds considered to be cross linking agents for the carboxyl group, i.e. carboxyl group blocking agents for treating the surface, and the vulcanization temperature (90 and 120° C.) affect the non-adhesion of latex film where an internally added aluminum type inorganic crosslinking agent is added to the latex were conducted. The test results are shown in Table 5.

Carboxyl group blocking agents for treating a surface (i.e., organic crosslinking agents for carboxyl groups):
(Example 20) polyamine triethylenetetramine(made by Wako Seiyaku)
(Example 21) melamine resin, Sumitex Resin M-3 (made by Sumitomo Kagaku Kogyo)
(Example 22) melamine resin, Sumirez Resin 613special (made by Sumitomo Kagaku Kogyo)
(Example 23) amino group-containing urethane resin, Superflex R-3000 (made by Daiichi Kagaku Kogyo)
(Example 24) blocked isocyanate prominate, XC-915 (made by Takeda Yakuhin Kogyo)
(Example 25) multifunctional epoxy compound, Denacol EX-614B (made by Nagase Kasei Kogyo)
(Example 26) epoxycresolnovolac resin emulsion, Denacol EM-150 (made by Nagase Kasei Kogyo)
(Example 27) bifunctional epoxy compound, Denacol EX-313 (made by Nagase Kasei Kogyo)

EXAMPLES 28 TO 36

In the same manner as in Examples 20 to 27, hydrogen bond formation regulators used in the field of paper, were tested to evaluate their performance as carboxyl group blocking agent. These compounds have been developed as waterproof endowing agent, printability improver, wet paper strength reinforcing agent and the like for paper, with their workability and safety taken into consideration. The results are shown in Table 6. As in the case of organic crosslinking agents for carboxyl groups, the compounds have a non-adhesive effect.

In Example 35, a test was conducted where an internally added aluminum type inorganic crosslinking agent, sodium aluminate, was not added.

Carboxyl group blocking agent for treating a surface (i.e., hydrogen bond formation regulators):
(Example 28) glyoxal (made by Wako Junyaku Co.)
(Example 29) polyamide resin, Sumirez Resin 5001 (made by Sumitomo Kagaku Kogyo Co.)
(Example 30) polyamide resin, Sunmide X-13A (made by Sanwa Kagaku Kogyo Co.)
(Example 31) polyamidepolyurea resin, Sumirez Resin 636 (made by Sumitomo Kagaku Kogyo Co.)
(Example 32) polyamideepoxy resin, Sumirez Resin 675 (made by Sumitomo Kagaku Kogyo Co.)
(Example 33) polyaminepolyurea resin, Sumirez Resin 302 (made by Sumitomo Kagaku Kogyo Co.)

TABLE 5

| Example No. | Carboxyl-group crosslinking organic agent for surface treatment | Trademark | Vulcanization temp. | Conc. of organic crosslinking agent | | | |
|---|---|---|---|---|---|---|---|
| | | | | 0.025% | 0.01% | 0.005% | 0.0025% |
| 20 | Polyamine | Triethyltetramine | 90° C. | ○ | | | |
| | | | 120° C. | Δ | | | |
| 21 | Melamine resin | Sumitex Resin M-3 | 90° C. | ○ | | | |
| | | | 120° C. | Δ | | | |
| 22 | Melamine resin | Sumitex Resin 613 special | 90° C. | ○ | | ○ | |
| | | | 120° C. | ○ | | | |
| 23 | Amino group-containing urethane resin | Superflex R-3000 (urethane) | 90° C. | ○ | | ○ | |
| | | | 120° C. | ○ | | | |
| 24 | Blocked isocyanate | Prominate XC-915 | 90° C. | ○ | | | |
| | | | 120° C. | ○ | | | |
| 25 | Polyfunctional epoxy compound | Denacol EX-614B | 90° C. | Δ | ○ | ○' | |
| | | | 120° C. | ○ | ○ | | |
| 26 | Epoxycresolnovolac resin | Denacol EM-150 | 90° C. | ○ | | | ○ |
| | | | 120° C. | ○ | | | ○ |
| 27 | Bifunctional epoxy compound | Denacol EX-313 | 90° C. | ○ | | ○ | |
| | | | 120° C. | ○ | | | |

(Example 34) polyaminepolyurea resin, PA-620 (made by Nippon PMC)
(Example 35) modified polyaminepolyurea resin, Sumirez Resin 712 (made by Sumitomo Kagaku Kogyo Co.)
(Example 36) polyamidepolyureaglyoxal condensation reaction product, Sumirez Resin 5004 (made by Sumitomo Kagaku Kogyo Co.)

EXAMPLE 40 TO 58

In the same manner as in Examples 20 to 39, the non-adhesion surfactants (cationic, amphoteric, nonionic, or anionic) were tested for their performance as carboxyl-group blocking agents, including a test for the effect of adding an internally added aluminum type inorganic crosslinking agent, sodium aluminate. The results are shown in Table 8.

TABLE 6

| Example No. | Hydrogen bond formation regulator for surface treatment | Trademark | Vulcanization temp. | Conc. of reactive organic compound | | | |
|---|---|---|---|---|---|---|---|
| | | | | 0.025% | 0.01% | 0.005% | 0.0025% |
| 28 | Glyoxal | | 90° C. | Δ | | | |
| | | | 120° C. | ○ | | | |
| 29 | Polyamide resin | Sumirez Resin 5001 | 90° C. | ○ | | ○ | ○ |
| | | | 120° C. | ○ | | | ○ |
| 30 | Polyamide resin | Sunmide X-13A | 90° C. | ○ | | | |
| | | | 120° C. | ○ | | | |
| 31 | Polyamide polyurea resin | Sumirez Resin 636 | 90° C. | ○ | | | ○ |
| | | | 120° C. | ○ | | | ○ |
| 32 | Polyamide epoxy resin | Sumirez Resin 675 | 90° C. | ○' | | | |
| | | | 120° C. | ○ | | | |
| 33 | Polyamine polyurea resin | Sumirez Resin 302 | 90° C. | ○ | | | ○' |
| | | | 120° C. | ○ | | | ○ |
| 34 | Polyamine polyurea resin | PA-620 | 90° C. | ○ | | | |
| | | | 120° C. | ○ | | | |
| 35 | Modified polyamine polyurea resin | Sumirez Resin 712 | 90° C. | ○ | | ○ | ○' |
| | | | 120° C. | ○ | | | ○' |
| | | NaAlO$_2$ not added | 90° C. | ○ | | | x |
| | | | 120° C. | ○ | | | x |
| 36 | Polyamidepolyureaglyoxal condensation reaction product | Sumirez Resin 5004 | 90° C. | ○ | ○' | ○ | |
| | | | 120° C. | ○ | | | |

EXAMPLES 37 TO 39

Tests were conducted in the same manner as in Examples 20 to 34 concerning a monofunctional carboxyl group blocking agent. The results are shown in Table 7. The agent, which is monofunctional, cannot crosslink a carboxyl group, and yet it has a non-adhesive effect. It is noted that blocking a carboxyl group and forming hydrophobicity are both important for the non-adhesion of the latex product.

Surface carboxyl blocking agents for treating a surface (i.e., monofunctional carboxyl blocking agents):
(Example 37) monofunctional modified bisphenol A type epoxy emulsion, Denacast EM-101 (made by Nagase Kasei Kogyo Co.)
(Example 38) monofunctional modified bisphenol A type epoxy emulsion, Denacast EM-103 (made by Nagse Kase Kogyo Co.)
(Example 39) monofunctional epoxy, Denacol EX-145 (made by Nagase Kasei Kogyo Co.)

Where sodium aluminate was not added, the non-adhesive effect of the surfactant is small.

Carboxyl group blocking agent for treating a surface (non-adhesive surfactant):
Non-adhesive Cationic Surfactant:
(Example 40) quarternary amine, Quartermin 86W (made by Kao Co.)
(Example 41) quarternary amine, Catinal MB 50A (made by Toho Kagaku Kogyo)
(Example 42) imidazoline type betaine, Anhitol 20YB (made by Kao)
(Example 43) oxide type betaine, Softamin L (made by Toho Kagaku Kogyo)
(Example 44) alkylamide type betaine, Ovazolin CAB-30 (made by Toho Kagaku Kogyo)
Non-adhesive Nonionic Surfactant:
(Example 45) tertiary amine, Esomin C/12 (made by Lion)
(Example 46) tertiary alkylamine, Amito 105 (made by Kao)
(Example 47) alkanolamide, Aminon PK-02S (made by Kao)

TABLE 7

| Example No. | Monofunctional carboxyl-group blocking agent for surface treatment | Trademark | Vulcanization temp. | Conc. of monofunctional carboxyl-group blocking agent | | | |
|---|---|---|---|---|---|---|---|
| | | | | 0.025% | 0.01% | 0.005% | 0.0025% |
| 37 | Monofunctional epoxy | Denacast EM-101 (emulsion) | 90° C. | ○ | | | |
| | | | 120° C. | ○ | | | |
| 38 | Monofunctional epoxy | Denacast EM-103 (emulsion) | 90° C. | ○ | | ○ | ○' |
| | | | 120° C. | ○ | | | ○ |
| 39 | Monofunctional epoxy | Denacol EX-145 | 90° C. | ○ | | | |
| | | | 120° C. | ○ | | | |

(Example 48) polyoxyethylenelauryether, Emulgen 109P (made by Kao)
(Example 49) polyoxyethylene derivative, Emulgen A60 (made by Kao)

Non-adhesive Anionic Surfactant:
(Example 50) β-naphthalenesulfonic acid formalin condensation product, Demol N (made by Kao)
(Example 51) alkylmethyltaurinate, Lipotac TE (made by Lion)
(Example 52) disodium dodecyldiphenylethersulfonic acid, Perex SS-L (made by Kao)

TABLE 8

| Example No. | Non-adhesive surfactant for surface treatment | | Trademark | Vulcanization temp. | Conc. of surfactant | | | |
|---|---|---|---|---|---|---|---|---|
| | | | | | 0.025% | 0.01% | 0.005% | 0.0025% |
| 40 | Cation | Quaternary amine | Quartermin 86W | 90° C. | ○ | | | |
| | | | | 120° C. | ○ | | | |
| | | | NaAlO$_2$ | 90° C. | x | | | |
| | | | not added | 120° C. | x | | | |
| 41 | Cation | Quaternary amine | Catinal MB-50A | 90° C. | ○' | | | ○' |
| | | | | 120° C. | ○ | | | ○ |
| | | | NaAlO$_2$ | 90° C. | x | | | x |
| | | | not added | 120° C. | x | | | x |
| 42 | Amphoteric | Imidazoline type betaine | Anhitol 20YB | 90° C. | ○ | ○' | Δ | |
| | | | | 120° C. | ○ | | | |
| | | | NaAlO$_2$ | 90° C. | x | x | x | x |
| | | | not added | 120° C. | x | | | Δ |
| 43 | Amphoteric | Oxide type betaine | Softamin L | 90° C. | Δ | | | ○ |
| | | | | 120° C. | ○ | | | ○ |
| | | | NaAlO$_2$ | 90° C. | x | | | x |
| | | | not added | 120° C. | x | | | x |
| 44 | Amphoteric | Alkylamide type betaine | Ovazolin CAB-30 | 90° C. | ○ | | ○ | |
| | | | | 120° C. | ○ | | | |
| | | | NaAlO$_2$ | 90° C. | x | | x | |
| | | | not added | 120° C. | x | | | |
| 45 | Nonion | Tertiary alkylamine | Esomin C/12 | 90° C. | ○' | | | ○' |
| | | | | 120° C. | ○ | | | ○ |
| | | | NaAlO$_2$ | 90° C. | x | | | x |
| | | | not added | 120° C. | x | | | x |
| 46 | Nonion | Tertiary alkylamine | Amito 105 | 90° C. | Δ | | | |
| | | | | 120° C. | ○ | | | |
| | | | NaAlO$_2$ | 90° C. | x | | | |
| | | | not added | 120° C. | x | | | |
| 47 | Nonion | Alkanolamide (lauryldiethanolamide) | Aminon PK-02S | 90° C. | ○ | ○ | Δ | |
| | | | | 120° C. | ○ | | | |
| | | | NaAlO$_2$ | 90° C. | x | x | x | |
| | | | not added | 120° C. | x | | | |
| 48 | Nonion | Polyoxyethylene laurylether | Emulgen 109P | 90° C. | Δ | | | |
| | | | | 120° C. | ○ | | | |
| | | | NaAlO$_2$ | 90° C. | x | | | |
| | | | not added | 120° C. | x | | | |
| 49 | Nonion | Polyoxyethylene derivative | Emulgen A60 | 90° C. | Δ | | | |
| | | | | 120° C. | ○ | | | |
| | | | NaAlO$_2$ | 90° C. | x | | | |
| | | | not added | 120° C. | x | | | |
| 50 | Anion | β-naphthalenesulfonic acid formalin condensation product | Demol N | 90° C. | ○ | | | ○' |
| | | | | 120° C. | ○ | | | ○ |
| | | | NaAlO$_2$ | 90° C. | x | | | x |
| | | | not added | 120° C. | x | | | x |
| 51 | Anion | Alkylmethyltaurinate | Lipotac TE | 90° C. | ○' | | | Δ |
| | | | | 120° C. | ○ | | | |
| | | | NaAlO$_2$ | 90° C. | x | | | x |
| | | | not added | 120° C. | x | | | x |
| 52 | Anion | Disodium dodecyldiphenylethersulfonate | Perex SS-L | 90° C. | Δ | | | |
| | | | | 120° C. | ○' | | | |
| | | | NaAlO$_2$ | 90° C. | x | | | |
| | | | not added | 120° C. | x | | | |

EXAMPLES 53 TO 58

To evaluate the performance of polymer type derivatives as carboxyl group blocking agents, tests were conducted in the same manner as in Examples 40 to 52. Although these compounds are sometimes treated as polymer surfactant, they were used as non-adhesive polymer type surfactants in the present invention. The results are shown in Table 9.

Carboxyl group blocking agent for treating a surface (i.e., non-adhesive polymer type surfactants):
(Example 53) cellulose derivative, Reoguard KGP (made by Lion)
(Example 54) cationized starch, CATO 308 (made by Nippon NSC)
(Example 55) cationized starch, Opti Bond 3282 (made by Nippon NSC)
(Example 56) dimethyldiallyammoniumchloride acrylamide copolymer, ME polymer 09W (made by Toho Kagaku Kogyo)
(Example 57) cationic polyurethane dispersion in water, F-8570D (made by Daiichi Kogyo Seiyaku)
(Example 58) ammonium polystyrenesulfonate, VERSA-TLYE915 (made by Nippon NSC)

(Example 61) alkylketene dimer, Hasize AK-720H (made by Harima Kasei)
(Example 62) styrene type synthetic sizing agent, BLS-720 (made by Misawa Ceramics)
(Example 63) olefin type synthetic sizing agent, Hamacoat AK-505 (made by Misawa Ceramics)
(Example 64) alkenyl succinate, Sizepine (made by Arakawa Kagaku Kogyo)

TABLE 10

| Example No. | Sizing agent for surface treatment | Trademark | Vulcan- ization temp. | Conc. of sizing agent 0.025% | 0.0025% |
|---|---|---|---|---|---|
| 59 | Fortified rosin sizing agent | Sizepine E-50 | 90° C. 120° C. | o o | |
| 60 | Emulsion type rosin sizing agent | Sizepine N-773 | 90° C. 120° C. | o o | o o |
| 61 | Alkylketene dimer | Hasize AK-720H NaAlO₂ not added | 90° C. 120° C. 90° C. 120° C. | o o o o | o o |

TABLE 9

| Example No. | | Non-adhesive polymer surfactant for surface treatment | Trademark | Vulcanization temp. | Conc. of polymer surfactant 0.025% | 0.01% | 0.005% | 0.0025% |
|---|---|---|---|---|---|---|---|---|
| 53 | Cation | Cellulose derivative | Reoguard KGP | 90° C. 120° C. | Δ o | | | |
| | | | NaAlO₂ not added | 90° C. 120° C. | x x | | | |
| 54 | Cation | Cationized starch | CATO 308 | 90° C. 120° C. | o o | | | Δ o' |
| | | | NaAlO₂ not added | 90° C. 120° C. | x x | | | |
| 55 | Cation | Cationized starch | Opti Bond 3282 | 90° C. 120° C. | o' o | | | |
| | | | NaAlO₂ not added | 90° C. 120° C. | x x | | | |
| 56 | Cation | Dimethyldiallylammonium chloride acrylamide copolymer | ME polymer 09W | 90° C. 120° C. | o' o | | | |
| | | | NaAlO₂ not added | 90° C. 120° C. | x x | | | |
| 57 | Cation | Cationic polyurethane dispersion in water | F-8570D | 90° C. 120° C. | o | | | |
| | | | NaAlO₂ not added | 90° C. 120° C. | x | | | |
| 58 | Anion | Ammonium polystrenesulforate | VERSA-TLYE915 | 90° C. 120° C. | Δ o | | | |
| | | | NaAlO₂ not added | 90° C. 120° C. | x x | | | |

EXAMPLES 59 TO 64)

To evaluate the performance of paper sizing agents as carboxyl group blocking agents, tests were conducted in the same manner as in Examples 20 to 39. The results are shown in Table 10. In Example 61, an internally added aluminum type inorganic crosslinking agent, sodium aluminate, was not added.

Carboxyl group blocking agent for treating a surface (i.e., sizing agent): (Example 59) fortified rosin, Sizepine E-50 (made by Arakawa Kagaku Kogyo). This sizing agent coagulates with a calcium salt. So, the treatment of the inside surface was conducted with Sizepine N-773 (concentration: 0.0025%) mentioned below, and the treatment of the outside surface was conducted with Sizepine E.
(Example 60) emulsion type rosin sizing agent, Sizepine N-773 (made by Arakawa Kagaku Kogyo).

TABLE 10-continued

| Example No. | Sizing agent for surface treatment | Trademark | Vulcan- ization temp. | Conc. of sizing agent 0.025% | 0.0025% |
|---|---|---|---|---|---|
| 62 | Styrene type synthetic sizing agent | BLS-720 | 90° C. 120° C. | o o | o o |
| 63 | Olefin type synthetic sizing agent | Hamacoat AK-505 | 90° C. 120° C. | o o | o' o |
| 64 | Alkenyl succinate | Sizepine S-400S | 90° C. 120° C. | o o | o o |

EXAMPLES 65 TO 81

Performance tests were conducted for carboxyl group blocking agents in the same manner as in Examples 20 to 64. The carboxyl-group blocking agents were directly added to the latex to confirm their effect. Accordingly, the latex film was immediately vulcanized after the leaching treatment to make each sample. An adhesion test was conducted according to adhesion test 2. The results are shown in Table 11. It is noted that any type of carboxyl group blocking agent for treating a surface is effective as an internally added carboxyl-group blocking agent. However, a carboxyl-group blocking agent that coagulates the latex when it is incorporated into a latex emulsion is not desirable. In these cases, it is necessary to take additional measures such as stabilizing the latex emulsion by adding a surfactant. Also studied was the effect of adding the internally added aluminum type inorganic crosslinking agent, sodium aluminate. In the case of a reactive carboxyl-group blocking agent (in Examples 70 and 77) and a carboxyl-group blocking agent which forms an insoluble salt with calcium ion (in Examples 76, 78 and 81), the non-adhesive effect occurs even when sodium aluminate is not added. When a polyamide polyurea resin (Sumirez Resin 703) is added, the latex emulsion coagulates if sodium aluminate is not added. However, when sodium aluminate is added, it disperses the Sumirez Resin 703 homogeneously. Thus, a non-adhesive effect is observed and coagulation of the emulsified latex is prevented.

Internally added carboxyl group blocking agents:
(Example 65) monofunctional modified bisphenol A type epoxy emulsion, Denacast EM-103 (made by Nagase Kasei Kogyo)
(Example 66) carbodiimide crosslinking agent, Carbodilite V-20 (made by Toyobo)
(Example 67) oxazoline crosslinking agent, Epocross W (made by Nihon Shokubai)
(Example 68) self-emulsifying type polyisocyanate, Aquanate 200 (made by Nihon Polyurethane Kogyo)
(Example 69) blocked isocyanate, Prominate XC-915 (made by Takeda Seiyaku)
(Example 70) polyamide resin, Sumirez Resin 5001 (made by Sumitomo Kagaku Kogyo)
(Example 71) polyamidepolyurea resin, Sumirez Resin 703 (made by Sumitomo Kagaku Kogyo)
(Example 72) β-naphthalenesulfonic acid formalin condensation product, Demol N (made by Kao)
(Example 73) alkylnaphthalenesulfonic acid formalin condensation polymerization product, Polyty N-100 (made by Lion)
(Example 74) alkylmethyltaurinate, Lipotac TE made by Lion)
(Example 75) emulsion type modified rosin sizing agent, Halfsize NES-650 (made by Harima Kasei)
(Example 76) fortified rosin sizing agent, Sizepine (made by Arakawa Kagaku Kogyo)
(Example 77) alkylketene dimer, Halfsize AK-720H (made by Harima Kasei)
(Example 78) alkenylsuccinate, Sizepine S-400S (made by Arakawa Kagaku Kogyo)
(Example 79) alkenylsuccinic acid anhydride, Colopearl Z-100S (made by Seiko Kagaku Kogyo)
(Example 80) styrene acryl type surface sizing agent, Colopearl M-150-2 (made by Seiko Kagaku Kogyo)
(Example 81) saponification product of an adduct of branched olefin and maleic anhydride, RFsize NSP-SH (made by Seiko Kagaku Kogyo)

TABLE 11

| Example No. | Internally added carboxyl-group blocking agent | Trademark | Vulcanization temp. | Amount added (part) 2.5 | 1.0 |
|---|---|---|---|---|---|
| 65 | Monofunctional epoxy | Denacast EM-103 | 90° C. | o' | x |
|  |  |  | 120° C. | o' | o |
|  |  | NaAlO₂ | 90° C. | x |  |
|  |  | not added | 120° C. | x |  |
| 66 | Carbodiimide | Carbodilite V-02 | 90° C. | o' | o' |
|  |  |  | 120° C. | o' | o |
|  |  | NaAlO₂ | 90° C. | x |  |
|  |  | not added | 120° C. | x |  |
| 67 | Oxazoline | Epocross W | 90° C. | o | o' |
|  |  |  | 120° C. | o | o |
|  |  | NaAlO₂ | 90° C. | x |  |
|  |  | not added | 120° C. | x |  |
| 68 | Self-emulsifying polyisocyanate | Aquanate 200 | 90° C. |  | o' |
|  |  |  | 120° C. |  | o |
|  |  | NaAlO₂ | 90° C. | x |  |
|  |  | not added | 120° C. | x |  |
| 69 | Blocked isocyanate | Prominate XC-915 | 90° C. |  | o |
|  |  |  | 120° C. |  | o |
|  |  | NaAlO₂ | 90° C. | x |  |
|  |  | not added | 120° C. | Δ |  |
| 70 | Polyamide resin | Sumirez Resin 5001 | 90° C. | o | o |
|  |  |  | 120° C. | o | o |
|  |  | NaAlO₂ | 90° C. | Δ |  |
|  |  | not added | 120° C. | o' |  |
| 71 | Polyamide polyurea resin | Sumirez Resin 703 | 90° C. | o | o' |
|  |  |  | 120° C. | o | o |
|  |  | NaAlO₂ | 90° C. | aggregate |  |
|  |  | not added | 120° C. |  |  |
| 72 | β-naphthalene-sulfonic acid formalin condensate | Demol N | 90° C. | o | o' |
|  |  |  | 120° C. | o | o |
|  |  | NaAlO₂ | 90° C. | x |  |
|  |  | not added | 120° C. | Δ |  |
| 73 | Alkylnaphthalene-sulfonic acid formalin condensate | Polyty N-100K | 90° C. |  | Δ |
|  |  |  | 120° C. |  | o |
|  |  | NaAlO₂ | 90° C. | x |  |
|  |  | not added | 120° C. | x |  |
| 74 | Alkylmethyl-taurinate | Lipotac TE | 90° C. | o | x |
|  |  |  | 120° C. | o | o |
|  |  | NaAlO₂ | 90° C. | x |  |
|  |  | not added | 120° C. | Δ |  |
| 75 | Emulsion type rosin sizing agent (modified rosin) | Hasize NES-650 | 90° C. | o' | Δ |
|  |  |  | 120° C. | o | o |
|  |  | NaAlO₂ | 90° C. | x |  |
|  |  | not added | 120° C. | Δ |  |
| 76 | Fortified rosin sizing agent | Sizepine E-50 | 90° C. | o | x |
|  |  |  | 120° C. | o | o |
|  |  | NaAlO₂ | 90° C. | Δ |  |
|  |  | not added | 120° C. | o' |  |
| 77 | Alkylketene dimer | Hasize AK-720H | 90° C. | o | o |
|  |  |  | 120° C. | o | o |
|  |  | NaAlO₂ | 90° C. | x |  |
|  |  | not added | 120° C. | o' |  |
| 78 | Alkenyl succinate | Sizepine S-400S | 90° C. | o | o' |
|  |  |  | 120° C. | o | o |
|  |  | NaAlO₂ | 90° C. | o' |  |
|  |  | not added | 120° C. | o |  |
| 79 | Alkenyl succinic acid anhydride | Coropearl Z-100S | 90° C. | o | o' |
|  |  |  | 120° C. | o | o |
|  |  | NaAlO₂ | 90° C. | x |  |
|  |  | not added | 120° C. | Δ |  |
| 80 | Styrene-acryl type surface sizing agent | Coropearl M-150-2 | 90° C. | o | Δ |
|  |  |  | 120° C. | o | o |
|  |  | NaAlO₂ | 90° C. | x |  |
|  |  | not added | 120° C. | Δ |  |
| 81 | Branched olefin-maleic anhydride adduct | RF size NSP-SH | 90° C. |  | Δ |
|  |  |  | 120° C. |  | o |
|  |  | NaAlO₂ | 90° C. | o' |  |
|  |  | not added | 120° C. | o |  |

EXAMPLES 82 TO 85

Fingerstalls were prepared in the same manner as in Example 29, except that internally added aluminum type inorganic crosslinking agents, as described below, were used in place of sodium aluminate. Adhesion and durability tests were conducted. The amount of internally added aluminum type inorganic crosslinking agent was 0.25 part $Al_2O_3$. The carboxyl-group blocking agent used was polyamide resin (Sumirez Resin 5001). The concentration of the polyamide resin for treating the surface was 0.025%. The results are shown in Table 12. As in the case of Example 29, the latex film was non-adhesive. Any fingerstall that did not break in the durability test, passed the test.

(Example 82) calcium aluminate (made by Soekawa Rikagaku)
(Example 83) magnesium aluminate (made by Soekawa Rikagaku)
(Example 84) aluminum magnesium hydroxide, Aluminum magnesium hydroxide 251 made by Tomita Seiyaku)
(Example 85) synthetic hydrotalcite, Synthetic hydrotalcite H (made by Tomita Seiyaku)

TABLE 12

| Example No. | Internally added aluminum type inorganic crosslinking agent | Trademark | Vulcanization temp. | Adhesion test 2 | Number of breakings |
|---|---|---|---|---|---|
| 82 | Calcium aluminate | | 90° C. | Δ | 0 |
| | | | 120° C. | ○ | 0 |
| 83 | Magnesium aluminate | | 90° C. | Δ | 0 |
| | | | 120° C. | ○ | 0 |
| 84 | Aluminum. magnesium hydroxide | Aluminum. magnesium hydroxide 251 | 90° C. | ○ | 0 |
| | | | 120° C. | ○ | 0 |
| 85 | Synthetic hydrotalcite | Synthetic hydrotalcite | 90° C. | ○' | 0 |
| | | | 120° C. | ○ | 0 |

EXAMPLE 86

In manufacturing fingerstalls in the same manner as in Examples 2 and 3, the dipping former was dipped and deposited with an external crosslinking agent for the inside surface, dried, and dipped in the methanolic external coagulant liquid 1 cm more deeply than the portion of the crosslinking agent and dried. Then, the former was dipped in the latex slightly more shallowly than the part of the methanolic external coagulation liquid. The former was then dipped in the external crosslinking liquid for the outside surface to the same depth as the external crosslinking agent for the inside surface. When these stalls are wound and then unwound, the adhesive portions remain wound as the rolled lip. In this case, since the latex is not directly brought into contact with the dipping former and since the thickness of the latex is increased due to the coagulation liquid, the removal of the latex film from the dipping former is easy and the winding is also easy.

EXAMPLE 87

In forming fingerstalls in the same manner as in Examples 14 and 86, the rolled lip was formed after the former was dipped in the latex but before exposure to an external crosslinking liquid. By then coating an external crosslinking liquid for the outer surface, non-adhesive fingerstalls with a rolled lip can be formed. In this case, even if the former is immersed in the external crosslinking liquid more deeply than the rolled lip portion, the rolled lip does not unwind and so it is not necessary to mind the depth of the external crosslinking liquid on the outer surface.

EXAMPLE 88

In forming fingerstalls in the same manner as in Example 4, the former was immersed in the latex more shallowly than the external coagulation liquid and the external crosslinking liquid to form a rolled lip. As in Example 86, since the latex has an increased thickness owing to the coagulation liquid, the removal of the latex film from the dipping former is easy and winding the fingerstall is also easy. If the latex is too dry when a rolled lip is formed, the rolled lip may unwind. But, if the rolled lip is made when the latex is half gelled and then dried, it does not unwind.

EXAMPLE 89

Fingerstalls were formed using the fingerstall manufacturing equipment (FIG. 2) under the same latex film forming conditions as used in screening carboxyl-group blocking agents. The former was immersed in the coagulation liquid and dried, and, thereafter, immersed in latex incorporated with 1.5 parts of zinc oxide, 0.25 part ($Al_2O_3$) of sodium aluminate and 1.5 parts of zinc oxide, and then dried. After being subjected to lip winding, leaching and drying, the former was immersed in an outside surface treating agent of 0.025% polyamide resin, Sumirez resin 5001 (made by Sumitomo Kagaku Kogyo) and dried at 90° C. for 2 minutes. Thereafter, winding and unwinding of the fingerstall were successively conducted. The film was dried at 90° C. for 3 minutes, again wound on the winding machine and removed from the former in the wound state. With inorganic outside-surface treating agents, a leaching treatment is necessary after immersion into the outside-surface treating agent. Since the present outside-surface treating agent is organic, the leaching treatment is unnecessary after the immersion into the outside-surface treating agent. Hence, the manufacturing steps can be reduced.

The stalls removed from the former were dried at 70° C. for 120 minutes to give the final products. The formed stalls were easy to don on the fingers.

EXAMPLE 90

Fingerstalls were formed in the same manner as in Example 86 except that the latex was incorporated with 1 part of alkylketene dimer, Halfsize AK-720H (made by Harima Kasei) as the carboxyl-group blocking agent. In this case, since the carboxyl-group blocking agent is added to the latex, it is not necessary to deposit the outside-surface treating agent after dipping the former into the latex. Hence, the manufacturing steps can be reduced. The manufacturing steps are as follows. The former is dipped in the coagulation liquid and dried, then dipped in the latex and dried, subjected to a leaching treatment after winding the mouth, and dried at 90° C. at 2 minutes. Thereafter, winding and unwinding were successively conducted, and the film was dried at 90° C. for 3 minutes. It was again wound on the winding machine and removed from the former in the wound state.

Fingerstalls removed from the former were dried at 70° C. for 120 minutes to give the final products. The stalls were easy to don on the fingers.

The following are examples of non-adhesive carboxylated latex products which have a layer treated with a carboxyl group blocking agent on the inside surface of the carboxylated latex products and whose outside surface has been chlorinated.

1. Preparation of a Raw Material Latex

A raw material latex (carboxylated NBR Nipol LX-551, made by Nippon Zeon) was added with 1.5 parts of activated zinc oxide and 0.25 part (as $Al_2O_3$) of aluminum hydroxide gel as the vulcanizing agent. The mixture was diluted with water or water and a carboxyl group blocking agent to adjust the concentration of solids to 22.5%.

2. Preparation of a Coagulant Solution

A coagulant aqueous solution of calcium nitrate tetrahydrate 300 g/1000 g was prepared. When the inside surface of the product was treated with a carboxyl group blocking agent, the carboxyl group blocking agent was added into the coagulant aqueous solution.

3. Formation of a Film of Carboxylated Synthetic Rubber Latex

A former, which had been dipped in the coagulant liquid and coated with the coagulant, was dipped into a liquid of the above-mentioned carboxylated synthetic rubber latex. After 5 seconds, a latex film was formed. The thickness of the latex film was 0.08 mm. The film was predried at 50° C. for 2 minutes and subjected to a leaching treatment at 75° C. for 3 minutes. Then, the film was dried at 90° C. for 1 minute, dipped into a chlorine aqueous solution having a chlorine concentration of 0.4 g for 5 seconds, and thereafter heated at 90° C. for 5 minutes. The latex film, thus prepared, was wound on the former and removed from the former. This sample was subjected to an adhesion test. The adhesion test was conducted by heating the sample, a wound film, at 90° C. for 30 minutes and unwinding after cooling. Cases where the unwinding was easy is denoted by 0; cases where the wound film could not be easily unwound to the end from the middle of the fingerstall is denoted by Δ; and cases where the unwinding was considerably difficult is denoted by x.

COMPARATIVE EXAMPLE 8

Under the above-mentioned conditions but without addition of the carboxyl group blocking agent either in the coagulant or in the latex, a latex film was prepared subjected only to a chlorination treatment on the outside surface. This latex film was put through the adhesion test. The results are shown in Table 13. The sample, after the adhesion test, was considerably difficult to unwind.

TABLE 13

| Comparative Example No. | Internally added carboxyl-group blocking agent and Carboxyl-group blocking agent for surface treatment | Adhesion Test |
|---|---|---|
| 8 | none | x |

EXAMPLE 91

The results of an adhesion test of a sample, obtained by adding in the latex a sizing agent as the carboxyl group blocking agent and chlorinating the outside surface, are shown in Table 14. The carboxyl group blocking agent used in the example is as follows.
(Example 91) Fortified rosin sizing agent Sizepine E-50 (made by Arakawa Kagaku Kogyo)

TABLE 14

| Example No. | Internally added carboxyl-group blocking agent | Trademark | Amount added (part) | Adhesion Test |
|---|---|---|---|---|
| 91 | Fortified rosin sizing | Sizepine E-50 | 2.5 | o |

EXAMPLES 92–94

The results of adhesion tests of samples, obtained by adding in the latex organic crosslinking agents as the carboxyl group blocking agent and chlorinating the outside surface, are shown in Table 15. The carboxyl group blocking agents used in the examples are as follows.

TABLE 15

| Example No. | Internally added carboxyl-group blocking agent | Trademark | Amount added (part) | Adhesion Test |
|---|---|---|---|---|
| 92 | Blocked isocyanate | Prominate XC-915 | 1 | o |
| 93 | Oxazorine | Epocross WS-500 | 2.5 | o |
| 94 | Monofunctional epoxy | Denacast EM-103 | 2.5 | o |

(Example 92) Blocked isocyanate Prominate XC-9 15 (made by Takeda Yakuhin
(Example 93) Oxazoline crosslinking agent Epocross WS-500 (made by Nippon Shokubai)
(Example 94) Monofunctional modified bisphenol A type epoxy emulsion Denacast EM-103 (Nagase Kasei Kogyo)

EXAMPLE 95

The results of an adhesion test of a sample, obtained by adding in the latex a surfactant as the carboxyl group blocking agent and chlorinating the outside surface, are shown in Table 16. The carboxyl group blocking agent used in the example is as follows.

TABLE 16

| Example No. | Internally added carboxyl-group blocking agent | Trademark | Amount added (part) | Adhesion Test |
|---|---|---|---|---|
| 95 | β-naphthalenesurufonic acid-formaline condensation product | demol N | 2.5 | o |

(Example 95) β-naphthalenesulfonic acid-formaline condensation product Demol N (made by Kao)

EXAMPLE 96

The results of an adhesion test of a sample, obtained by adding in the latex a hydrogen bond forming regulator as the carboxyl group blocking agent and chlorinating the outside surface, are shown in Table 17. The carboxyl group blocking agent used in the example is as follows.
(Example 96) Polyamidepolyurea resin Sumirez Resin 703 (made by Sumitomo Kagaku)

TABLE 17

| Example No. | Internally added carboxyl-group blocking agent | Trademark | Amount added (part) | Adhesion Test |
|---|---|---|---|---|
| 96 | Polyamide polyurea resin | Sumirez resin 703 | 2.5 | o |

EXAMPLE 97

The results of an adhesion test of a sample, obtained by using a sizing agent as the carboxyl group blocking agent for treating the inside surface and by chlorinating the outside surface, are shown in Table 18. The carboxyl group blocking agent used in the example is as follows.

(Example 97) Alkylketene dimer Hasize AK-720H (made by Harima Kasei)

TABLE 18

| Example No. | Carboxyl-group blocking agent for surface treatment | Trademark | Concentration (%) | Adhesion Test |
|---|---|---|---|---|
| 97 | Alkylketen dimer | Hasize AK-720H | 0.025 | ○ |

EXAMPLE 98

The results of an adhesion test of a sample, obtained by using an organic crosslinking agent as the carboxyl group blocking agent for treating the inside surface and chlorinating the outside surface, are shown in Table 19. The carboxyl group blocking agent used in the example is as follows.

(Example 98) Blocked isocyanate Prominate XC-915 (made by Takeda Yakuhin Kogyo)

TABLE 19

| Example No. | Carboxyl-group blocking agent for surface treatment | Trademark | Concentration (%) | Adhesion Test |
|---|---|---|---|---|
| 98 | Blocked isocyanate | Prominate XC-915 | 0.025 | ○ |

EXAMPLE 99

The results of an adhesion test of a sample, obtained by using a hydrogen bond forming regulator as the carboxyl group blocking agent for treating the inside surface and chlorinating the outside surface, are shown in Table 20. The carboxyl group blocking agent used in the example is as follows.

(Example 99) Polyamide resin Sumirez Resin 5001 (made by Sumitomo Kagaku)

TABLE 20

| Example No. | Carboxyl-group blocking agent for surface treatment | Trademark | Concentration (%) | Adhesion Test |
|---|---|---|---|---|
| 99 | Polyamide resin | Sumirez resin 5001 | 0.025 | ○ |

EXAMPLE 100

The results of an adhesion test of a sample, obtained by using an aluminum compound as the carboxyl group blocking agent for treating the inside surface and chlorinating the outside surface, are shown in Table 21. The carboxyl group blocking agent used in the example is as follows.

(Example 100) Polyaluminumhydroxide Paho#2S (made by Asada Kagaku Kogyo)

TABLE 21

| Example No. | Carboxyl-group blocking agent for surface treatment | Trademark | Concentration (%) | Adhesion Test |
|---|---|---|---|---|
| 100 | Polyaluminum hydroxide chloride | Paho#2S | 0.025 | ○ |

As shown in the above examples, all the carboxylated latex films made according to the present invention were non-adhesive.

Industrial Applicability

The present invention provides a powder-free, non-adhesive latex product obtained by adding a carboxyl-group blocking agent into a carboxylated latex, or, alternatively, by providing a layer treated with the carboxyl-group blocking agent to one or both surfaces of the carboxylated latex product. The present invention also enables for the manufacture of a non-adhesive latex product having excellent durability if the carboxylated contains an internally added aluminum type inorganic crosslinking agent, such as aluminate or aluminum hydroxide gel. In the case of a fingerstall, a non-powdered machine wound product can be prepared on-machine by utilizing the non-adhesive product.

What is claimed is:

1. A non-adhesive and durable carboxylated latex product with inner surface and/or outer surface treated with an external carboxyl-group blocking agent comprising a non-adhesive cationic metal ion crosslinking agent having three or more valences, wherein the carboxylated latex is internally added with anionic aluminate salt or nonionic aluminum hydroxide gel.

2. The non-adhesive and durable carboxylated latex product according to claim 1, wherein the cationic metal ion crosslinking agent is an aluminum compound, a titanium compound, a zirconium compound or any combination thereof.

3. A non-adhesive and durable carboxylated latex product with inner surface and/or outer surface treated with an external carboxyl-group blocking agent comprising a non-adhesive organic crosslinking agent for a carboxyl group of the carboxylated latex, wherein the carboxylated latex, wherein the carboxylated latex is internally added with anionic aluminate salt or nonionic aluminum hydroxide gel.

4. The non-adhesive and durable carboxylated latex product according to claim 3, wherein the non-adhesive organic crosslinking agent for the carboxyl comprises an aziridine compound, an epoxy compound, a blocked isocyanate, an oxazoline compound, a carbodiimido compound, a melamine formaldehyde resin, an ureaformaldehyde resin, an isocyanate, a phenolformaldehyde resin, a glycol, a polyol, a diamine, a polyamine, a hexamethoxymethylmelanine, a methylolacrylamide, or any combination thereof.

5. A non-adhesive and durable carboxylated latex product with inner surface and/or outer surface treated with an external carboxyl-group blocking agent comprising a compound selected from the group consisting of glyoxals, polyamide compounds, polyamide polyurea compounds, polyamine polyurea compounds, polyamideamine polyurea compounds, polyamide polyurea glyoxal condensation reaction products, polyamideamine compounds, polyamideamine epihalohydrine condensation reaction products, polyamideamine formaldehyde condensation reaction products, polyamine epihalohydrine condensation reaction products, polyamine formaldehyde condensation reaction products, polyamine polyurea epihalohydrine condensation reaction products, polyamide polyurea formaldehyde condensation reaction products, polyamine polyurea epihalohydrine condensation reaction products, polyamine polyurea formaldehyde condensation reaction products, polyamideamine polyurea epihalohydrine condensation reaction products, polyamideamine polyurea formaldehyde condensation reaction products, and combinations thereof, wherein the carboxylated latex is internally added with anionic aluminate salt or nonionic aluminum hydroxide gel.

6. A non-adhesive and durable carboxylated latex product with inner surface and/or outer surface treated with an external carboxyl-group blocking agent comprising a compound selected from the group consisting of monofunctional amines, monofunctional epoxy compounds, monofunctional isocyanates, monofunctional blocked isocyanates, and combinations thereof, wherein the carboxylated latex is internally added with anionic aluminate salt or nonionic aluminum hydroxide gel.

7. A non-adhesive and durable carboxylated latex product with inner surface and/or outer surface treated with an external carboxyl-group blocking agentcomprising a non-adhesive sizing agent, wherein the carboxylated latex is internally added with anionic aluminate salt or nonionic aluminum hydroxide gel.

8. A non-adhesive and durable carboxylated latex product with inner surface and/or outer surface treated with an external carboxyl-group blocking agent comprising a non-adhesive surfactant, wherein the carboxylated latex is internally added with anionic aluminate salt or nonionic aluminum hydroxide gel.

9. A non-adhesive and durable carboxylated latex product with inner surface and/or outer surface treated with external carboxyl-group blocking agent according to any one of claims 1 to 8, wherein the carboxylated latex is internally added and treated with anionic aluminate salt or nonionic aluminum hydroxide gel and any one or more of a non-adhesive internal carboxyl-group blocking agent comprising a non-adhesive aziridine compound, a non-adhesive epoxy compound, a non-adhesive blocked isocyanate, a non-adhesive oxazoline compound, a non-adhesive carbodiimido compound, a non-adhesive melamineformaldehyde resin, a non-adhesive ureaformaldehyde resine, a non-adhesive isocyanate, a non-adhesive phenolformaldehyde resin, a non-adhesive glycol, a non-adhesive polyol, a non-adhesive diamine, a non-adhesive polyamine, a non-adhesive hexamethoxymethylmelamine, a non-adhesive methylolacrylamide, glycoxals, non-adhesive polyamide compounds, non-adhesive polyamide polyurea compounds, non-adhesive polyamine polyurea compounds, non-adhesive polyamideamine polyurea compounds, non-adhesive polyamide polyurea glyoxal condensation reaction products, non-adhesive polyamideamine compounds, non-adhesive polyamideamine epihalohydrine condensation reaction products, non-adhesive polyamideamine formaldehyde condensation reaction products, non-adhesive polyamine epihalohydrine condensation reaction products, non-adhesive polyamine formaldehyde condensation reaction products, non-adhesive polyamide polyurea epihalohydrine condensation reaction products, non-adhesive polyamide polyurea formaldehyde condensation reaction products, non-adhesive polyamine polyurea epihalohydrine condensation reaction products, non-adhesive polyamideamine polyurea epihalohyrine condensation reaction products, non-adhesive polyamideamine polyurea formaldehyde condensation reaction products, non-adhesive monofunctional amines, non-adhesive monofunctional epoxy compounds, non-adhesive monofunctional isocyanates and non-adhesive monofunctional blocked-isocyanates, a non-adhesive sizing agent, beta-naphthalen-sulfonic acid formalin condensates,alkynaphthalene-sulfonic acid formaline condensates and/or allkylmethyl taurinates.

* * * * *

UNITED STATES PATENT AND TRADEMARK OFFICE
CERTIFICATE OF CORRECTION

| | |
|---|---|
| PATENT NO. | : 6,939,617 B2 |
| DATED | : September 6, 2005 |
| INVENTOR(S) | : Kazuo Koide, Takayuki Suzuki and Takahisa Suzuki |

It is certified that error appears in the above-identified patent and that said Letters Patent is hereby corrected as shown below:

Column 28,
Lines 57 and 66, replace "hydroxide chloride" with -- "hydroxide --.

Column 30,
Line 26, replace "chloride in Example 16" with -- in Example 16 --;
Line 32, replace "hydroxide chloride" with -- "hydroxide --.

Column 31,
Line 3, replace "hydroxide chloride" with -- "hydroxide --.
Table 3, under Example No. 16, replace "hydroxide chloride" with
-- "hydroxide --.

Column 48,
Table 21, under Example No. 100, replace "hydroxide chloride" with -- "hydroxide --.
Line 41, should read as follows:
-- 3. A non-adhesive and durable carboxylated latex product with inner surface and/or outer surface treated with an external carboxyl-group blocking agent comprising a non-adhesive organic crosslinking agent for a carboxyl group of the carboxylated latex, wherein the carboxylated latex is internally added with anionic aluminate salt or nonionic aluminum hydroxide gel. --.
Line 58, should read:
-- 5. A non-adhesive and durable carboxylated latex product with inner surface and/or outer surface treated with an external carboxyl-group blocking agent comprising a compound selected from the group consisting of glyoxals, polyamide compounds, polyamide polyurea compounds, polyamine polyurea compounds, polyamideamine polyurea compounds, polyamide polyurea glyoxal condensation reaction products, polyamideamine compounds, polyamideamine epihalohydrine condensation reaction products, polyamideamine formaldehyde condensation reaction products, polyamine epihalohydrine condensation reaction products, polyamine formaldehyde condensation reaction products, polyamine polyurea epihalohydrine condensation reaction products, polyamide polyurea formaldehyde condensation reaction products, polyamine polyurea formaldehyde condensation reaction products, polyamideamine polyurea epihalohydrine condensation reaction products, polyamideamine polyurea formaldehyde condensation reaction products, and combinations thereof, wherein the carboxylated latex is internally added with anionic aluminate salt or nonionic aluminum hydroxide gel. --.

UNITED STATES PATENT AND TRADEMARK OFFICE
CERTIFICATE OF CORRECTION

PATENT NO. : 6,939,617 B2
DATED : September 6, 2005
INVENTOR(S) : Kazuo Koide, Takayuki Suzuki and Takahisa Suzuki It is certified that error appears in the above-identified patent and that said Letters Patent is hereby corrected as shown below:

<u>Column 49,</u>
Line 22, should read:
-- 7. A non-adhesive and durable carboxylated latex product with inner surface and/or outer surface treated with an external carboxyl-group blocking agent comprising a non-adhesive sizing agent, wherein the carboxylated latex is internally added with anionic aluminate salt or nonionic aluminum hydroxide gel. --.

Signed and Sealed this

Ninth Day of May, 2006

JON W. DUDAS
*Director of the United States Patent and Trademark Office*